US012592319B1

(12) United States Patent
Shorter et al.

(10) Patent No.: US 12,592,319 B1
(45) Date of Patent: Mar. 31, 2026

(54) EARLY PREDICTION OF CLINICAL TRIAL SIGNALS

(71) Applicant: IQVIA Inc., Parsippany, NJ (US)

(72) Inventors: Gary Shorter, Cary, NC (US); Naouel Baili Benabdallah, Cary, NC (US); Brian Slocum Vannah, Denver, CO (US)

(73) Assignee: IQVIA Inc., Parsippany, NJ (US)

( * ) Notice: Subject to any disclaimer, the term of this patent is extended or adjusted under 35 U.S.C. 154(b) by 26 days.

(21) Appl. No.: 18/613,886

(22) Filed: Mar. 22, 2024

Related U.S. Application Data

(60) Provisional application No. 63/454,555, filed on Mar. 24, 2023.

(51) Int. Cl.
| | |
|---|---|
| *G16H 50/70* | (2018.01) |
| *G16H 10/20* | (2018.01) |
| *G16H 50/20* | (2018.01) |
| *G16H 50/30* | (2018.01) |

(52) U.S. Cl.
CPC ............. *G16H 50/20* (2018.01); *G16H 10/20* (2018.01); *G16H 50/70* (2018.01)

(58) Field of Classification Search
CPC ......... G16H 50/70; G16H 10/60; G16H 10/20
See application file for complete search history.

(56) References Cited

U.S. PATENT DOCUMENTS

2020/0211716 A1* 7/2020 Lefkofsky ............. G06F 18/214
2024/0312575 A1* 9/2024 Liu ........................ G16H 50/20

FOREIGN PATENT DOCUMENTS

WO      WO-2019144116 A1 *   7/2019   ............. G16H 20/00

OTHER PUBLICATIONS

Jering, Karola S., et al. "Improving clinical trial efficiency using a machine learning-based risk score to enrich study populations." European Journal of Heart Failure 24.8 (2022): 1418-1426. (Year: 2022).* saedsayad.com [online], "Decision Tree Regression," available on or before Jun. 2, 2023, via Internet Archive: Wayback Machine URL <https://web.archive.org/web/20230602213253/https://www.saedsayad.com/decision_tree_reg.htm>, retrieved on Mar. 19, 2025, retrieved from URL <https://www.saedsayad.com/decision_tree_reg.htm>, 5 pages.

* cited by examiner

*Primary Examiner* — Jason B Dunham
*Assistant Examiner* — Constantine Siozopoulos
(74) *Attorney, Agent, or Firm* — ALG Intellectual Property, LLC

(57) ABSTRACT

Methods and systems including computer programs encoded on computer storage media, for a method for detecting signals related to subjects participating in a clinical trial. In some implementations, a computer collects clinical data from multiple sources. The computer standardizes and redacts personally identifiable information and determines predictive features that correspond to characteristics of the data that correlate with efficacy and safety signals. The computer obtains training data and trains machine learning models to predict one or both of a predicted efficacy signal and a predicted safety signal for a subject. The computer receives clinical data for a particular clinical trial subject enrolled in an ongoing clinical trial and predicts one or more signals and receives a review of the signals through a user interface. The computer updates the predictive components of the system based on the review.

20 Claims, 21 Drawing Sheets

Clinical Trial Subject 104

Clinical Trial Site 102

Prediction Module 106

Clinical Trial Reviewer 108

Clinical Trial Review Center 110

100

Model Outlier Analysis (112)
Clinical Trial Subject Profiling (114)
Medical review findings analysis (116)
Cluster analysis (118)
Clinical trial subject subgroup analysis (120)

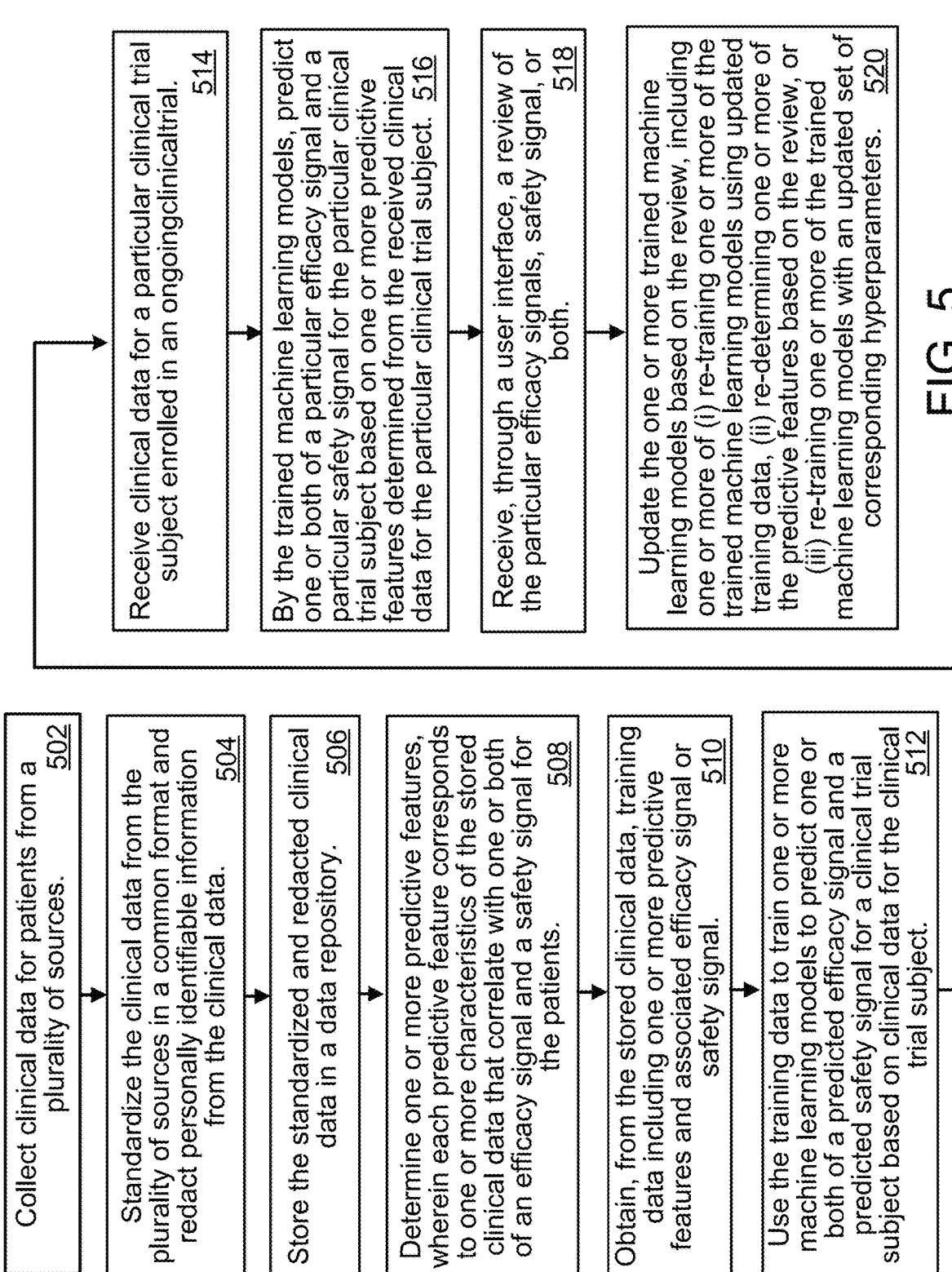

FIG. 5

Collect clinical data for patients from a plurality of sources.  502

Standardize the clinical data from the plurality of sources in a common format and redact personally identifiable information from the clinical data.  504

Store the standardized and redacted clinical data in a data repository.  506

Determine one or more predictive features, wherein each predictive feature corresponds to one or more characteristics of the stored clinical data that correlate with one or both of an efficacy signal and a safety signal for the patients.  508

Obtain, from the stored clinical data, training data including one or more predictive features and associated efficacy signal or safety signal.  510

Use the training data to train one or more machine learning models to predict one or both of a predicted efficacy signal and a predicted safety signal for a clinical trial subject based on clinical data for the clinical trial subject.  512

Receive clinical data for a particular clinical trial subject enrolled in an ongoingclinicaltrial.  514

By the trained machine learning models, predict one or both of a particular efficacy signal and a particular safety signal for the particular clinical trial subject based on one or more predictive features determined from the received clinical data for the particular clinical trial subject.  516

Receive, through a user interface, a review of the particular efficacy signals, safety signal, or both.  518

Update the one or more trained machine learning models based on the review, including one or more of (i) re-training one or more of the trained machine learning models using updated training data, (ii) re-determining one or more of the predictive features based on the review, or (iii) re-training one or more of the trained machine learning models with an updated set of corresponding hyperparameters.  520

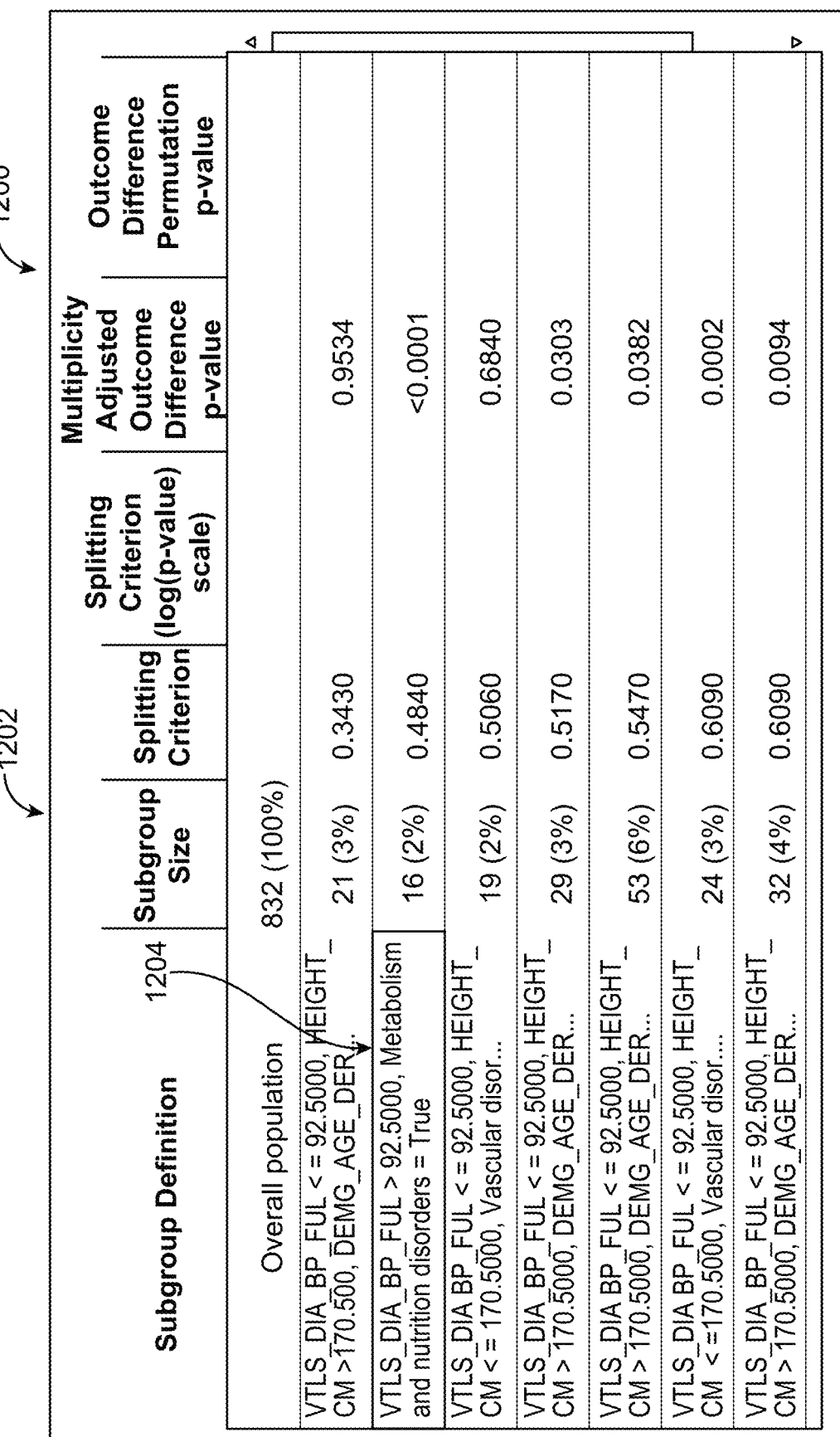

| Subgroup Definition | Subgroup Size | Splitting Criterion | Splitting Criterion (log(p-value) scale) | Multiplicity Adjusted Outcome Difference p-value | Outcome Difference Permutation p-value |
|---|---|---|---|---|---|
| Overall population | 832 (100%) | | | | |
| VTLS_DIA_BP_FUL <= 92.5000, HEIGHT_ CM >170.500, DEMG_AGE_DER... | 21 (3%) | 0.3430 | | 0.9534 | |
| VTLS_DIA_BP_FUL > 92.5000, Metabolism and nutrition disorders = True | 16 (2%) | 0.4840 | | <0.0001 | |
| VTLS_DIA_BP_FUL <= 92.5000, HEIGHT_ CM <=170.5000, Vascular disor... | 19 (2%) | 0.5060 | | 0.6840 | |
| VTLS_DIA_BP_FUL > 92.5000, HEIGHT_ CM >170.5000, DEMG_AGE_DER... | 29 (3%) | 0.5170 | | 0.0303 | |
| VTLS_DIA_BP_FUL > 92.5000, HEIGHT_ CM >170.5000, DEMG_AGE_DER... | 53 (6%) | 0.5470 | | 0.0382 | |
| VTLS_DIA_BP_FUL <=92.5000, HEIGHT_ CM <=170.5000, Vascular disor.... | 24 (3%) | 0.6090 | | 0.0002 | |
| VTLS_DIA_BP_FUL > 92.5000, HEIGHT_ CM >170.5000, DEMG_AGE_DER... | 32 (4%) | 0.6090 | | 0.0094 | |

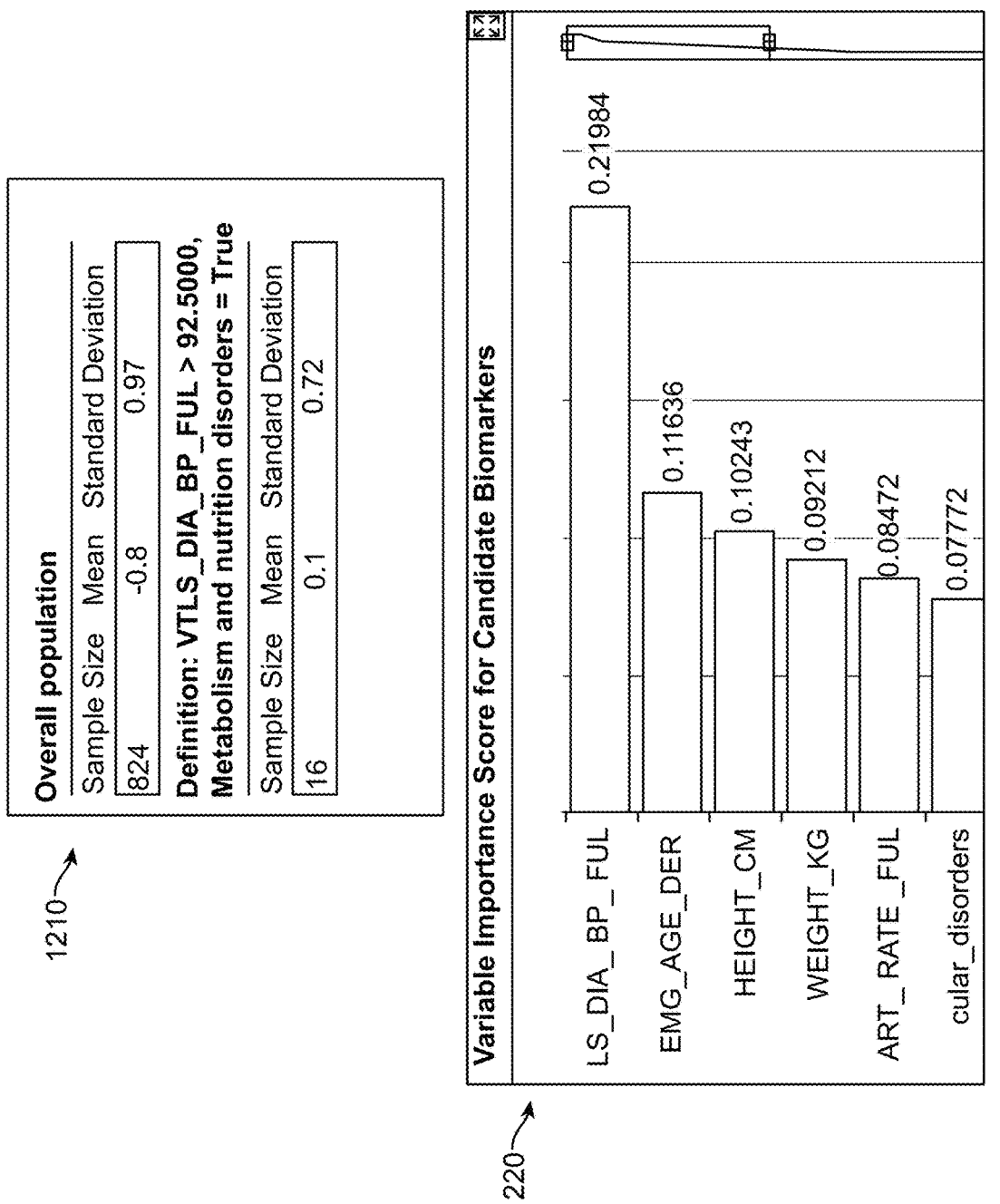
FIG. 12 (Cont. 1)

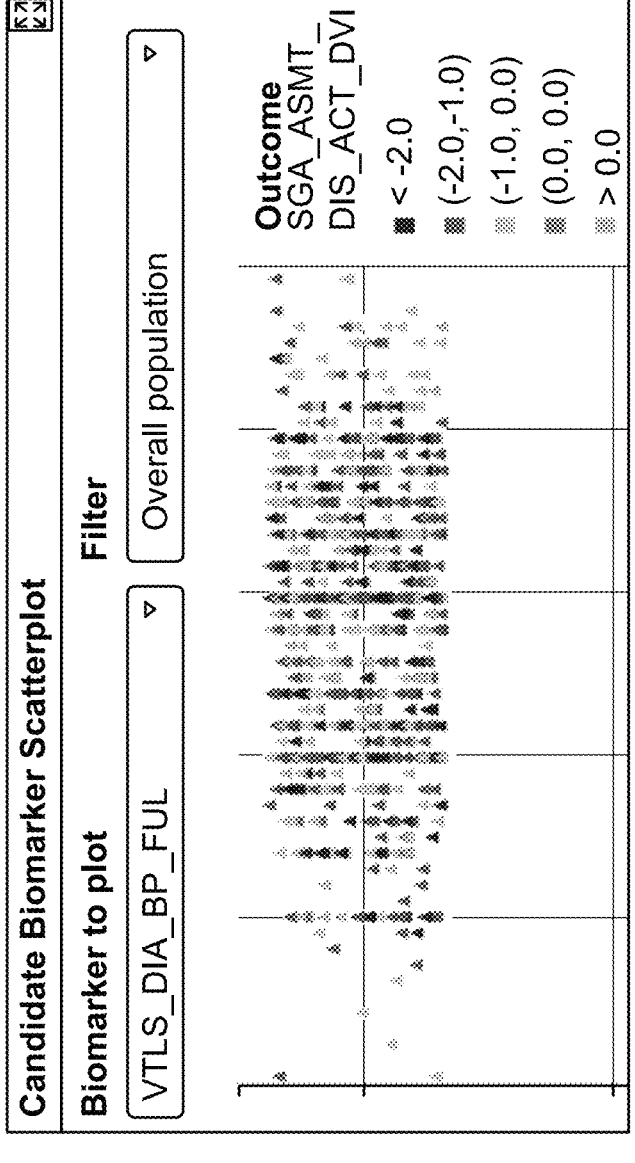
FIG. 12 (Cont. 2)

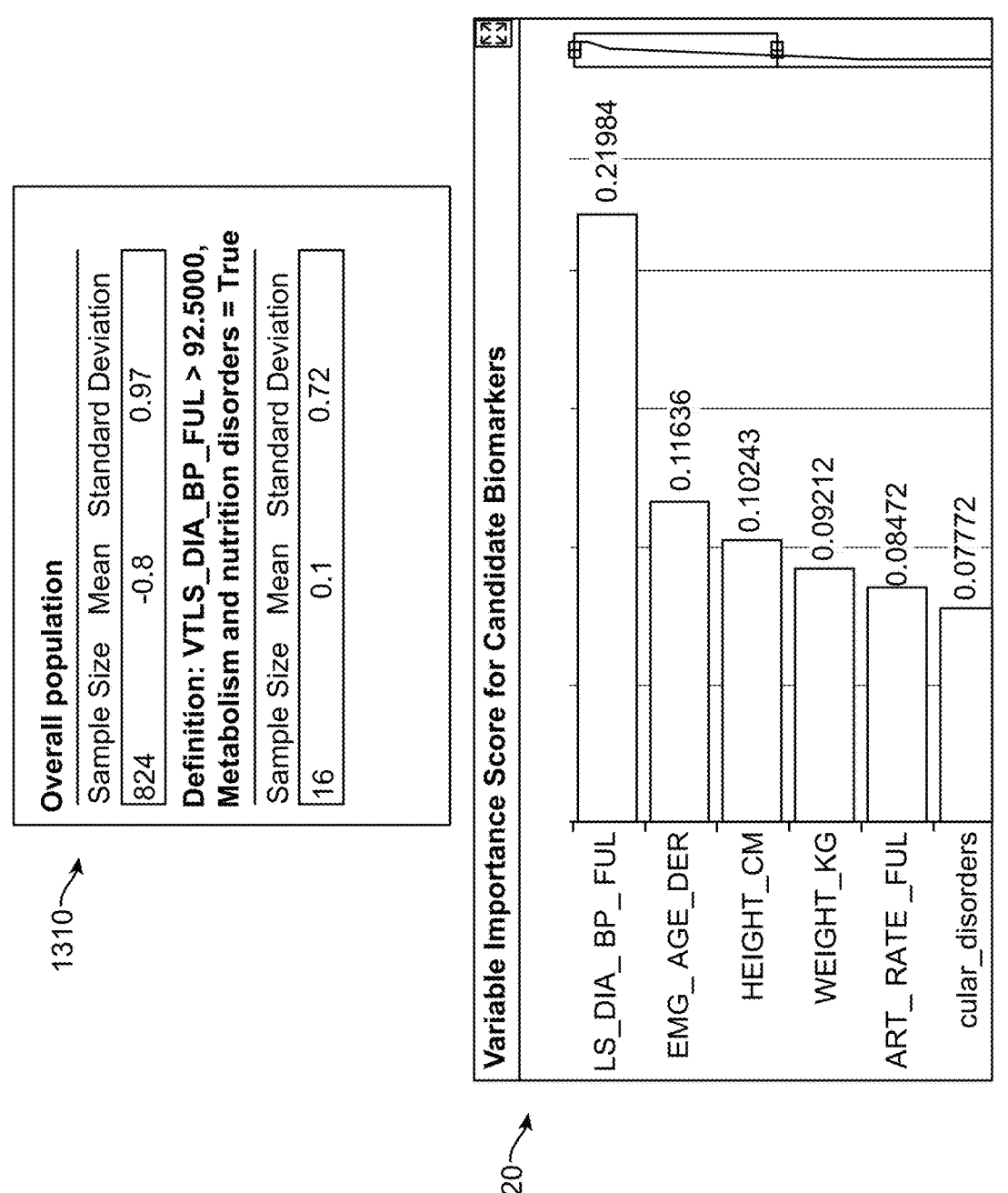
FIG. 13 (Cont. 1)

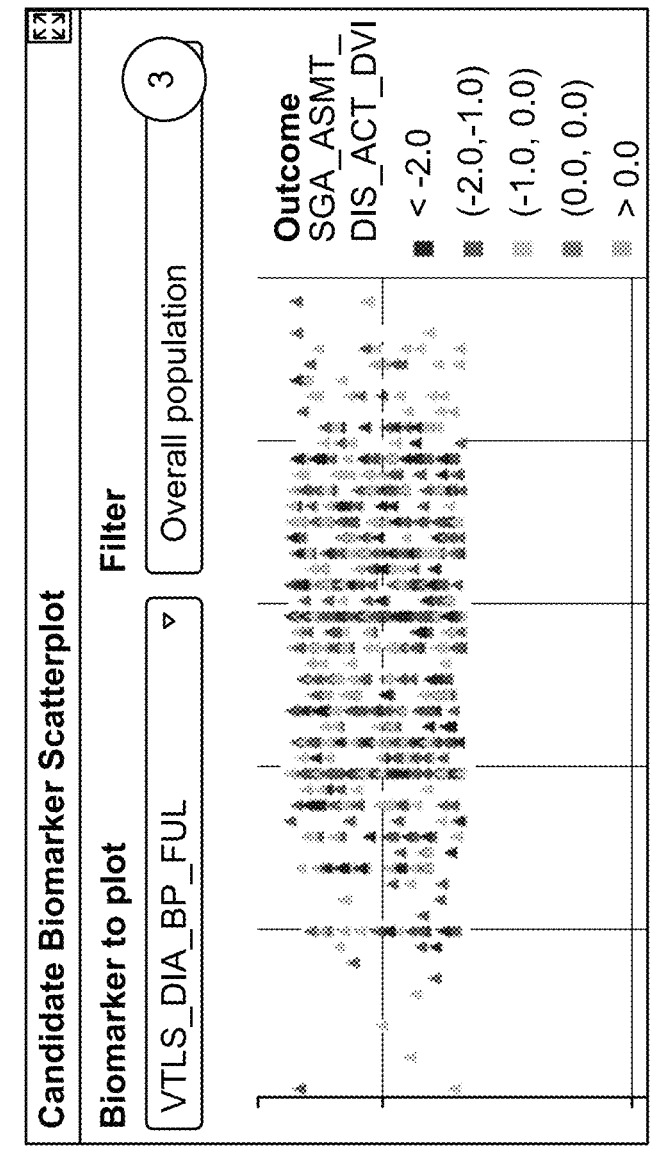
FIG. 13 (Cont. 2)

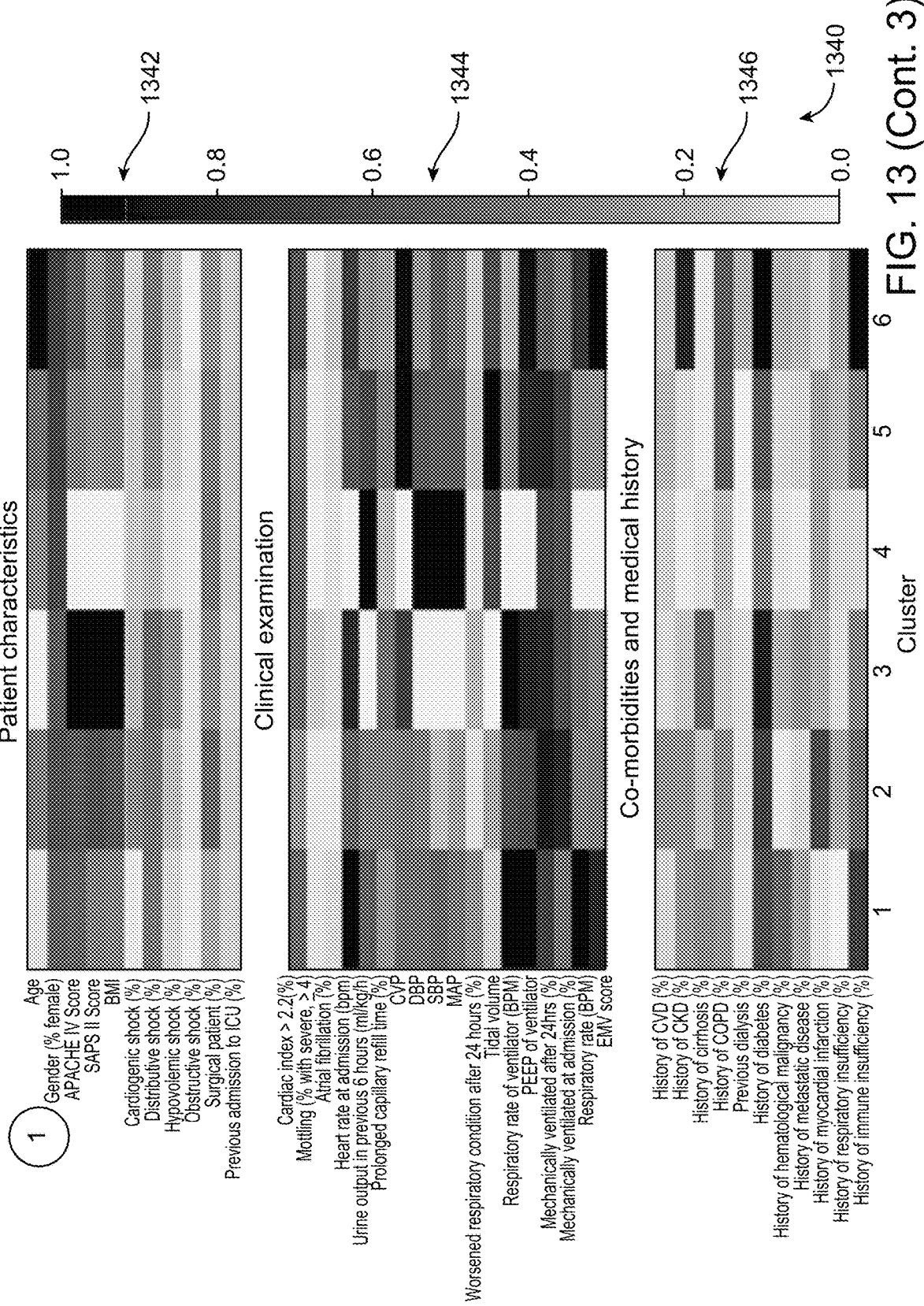
FIG. 13 (Cont. 3)

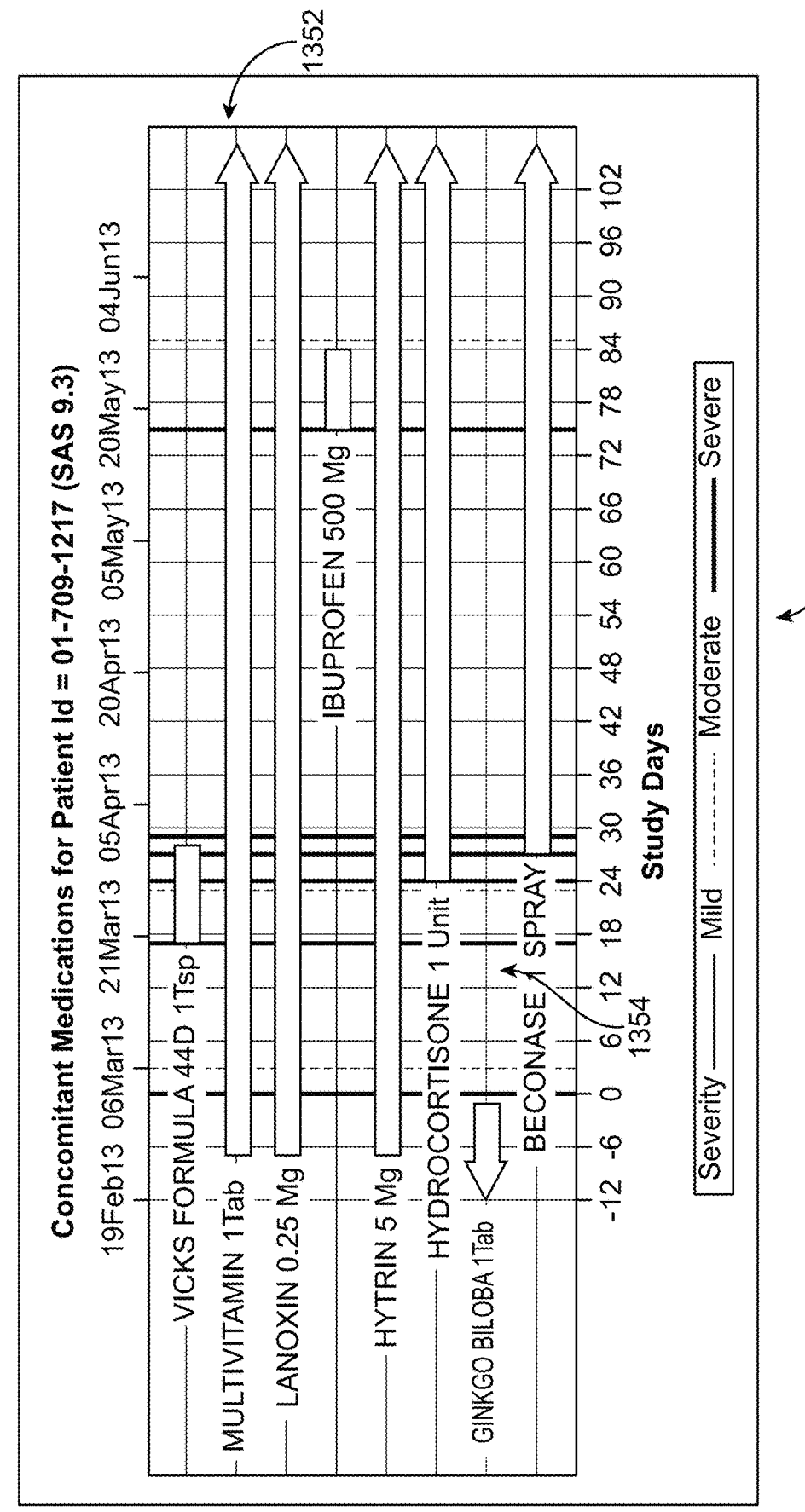
FIG. 13 (Cont. 4)

| Model Type | Description | Precision | Sensitivity | F1 | Accuracy |
|---|---|---|---|---|---|
| CaRT Tree 1420 | Demographics, vitals, medical history, con-meds, pain scores, NIS | .55 | .18 | .27 | .65 |
| CaRT RF 1422 | Above static information + pain scores from first n visits | .80 | .27 | .39 | .75 |
| CaRT RF 1424 | Above static information + change in pain from baseline to first n visits | .68 | .75 | .71 | .73 |

FIG. 14

| Model Type | Description | Precision | Sensitivity | F1 | Accuracy |
|---|---|---|---|---|---|
| CaRT RF <u>1522</u> | Demographics, vitals, medical history, con-meds, pain scores, NIS + change in pain from baseline to first n visits | .61 | .11 | .18 | .65 |
| CaRT RF <u>1524</u> | Demographics, vitals, medical history, con-meds, pain scores, NIS + change in pain from baseline to first n visits. Only 1Tree | .52 | .50 | .51 | .65 |

FIG. 15

EARLY PREDICTION OF CLINICAL TRIAL SIGNALS

CROSS-REFERENCE TO RELATED APPLICATIONS

This application claims the benefit under 35 U.S.C. § 119(e) of the filing date of U.S. Patent Application No. 63/454,555, filed Mar. 24, 2023, entitled "SMART CLINICAL SIGNAL DETECTOR," which is incorporated herein by reference in its entirety.

BACKGROUND

A clinical trial prospectively assigns human participants/ subjects or groups of human subjects to one or more health-related interventions to evaluate the effects of those interventions on health outcomes.

SUMMARY

The systems and techniques described here relate to the early prediction of signals related to the safety (e.g., adverse events) and/or efficacy of a treatment for a clinical trial subject associated with a clinical trial. Adverse events occur when a subject experiences an undesirable medical occurrence, which may be caused by or correlated with the medical treatment being evaluated in the trial. These events can range from mild symptoms to serious conditions that can significantly impact the subject's health. The proposed methods include training machine learning models and iterative updating of the machine learning models to identify potential adverse events at the earliest possible stage. This proactive approach allows for timely intervention, potentially mitigating the severity of the adverse events, enhancing patient safety, and improving the overall integrity of the clinical trial.

In one aspect, a method for detecting signals related to subjects participating in a clinical trial includes collecting clinical data for patients from multiple sources, standardizing the clinical data from the multiple sources in a common format and redacting personally identifiable information from the clinical data, and storing the standardized and redacted clinical data in a data repository.

The method includes determining one or more predictive features, where each predictive feature corresponds to one or more characteristics of the stored clinical data that correlate with one or both of an efficacy signal and a safety signal for the patients.

The method further includes obtaining, from the stored clinical data, training data including one or more predictive features and associated efficacy signal or safety signal and using the training data to train one or more machine learning models to predict one or both of a predicted efficacy signal and a predicted safety signal for a clinical trial subject based on clinical data for the clinical trial subject.

The method includes receiving clinical data for a particular clinical trial subject enrolled in an ongoing clinical trial and by the trained machine learning models, predicting one or both of a particular efficacy signal and a particular safety signal for the particular clinical trial subject based on one or more predictive features determined from the received clinical data for the particular clinical trial subject. The method includes receiving, through a user interface, a review of the particular efficacy signals, safety signal, or both, and updating the one or more trained machine learning models based on the review, including one or more of (i) re-training one or more of the trained machine learning models using updated training data, (ii) re-determining one or more of the predictive features based on the review, or (iii) re-training one or more of the trained machine learning models with an updated set of corresponding hyperparameters.

Implementations may include any or all of the following features. The method including determining one or more of the predictive features by identifying one or more characteristics of the stored clinical data that correlate with one or both of an efficacy signal and a safety signal associated with a population of clinical trial subjects. The characteristics including one or more biomarkers. The method in which re-determining the one or more predictive features includes updating a relative importance of one or more predictive features compared to the other predictive features. The method in which re-training one or more of the trained machine learning models with an updated set of corresponding hyperparameters includes implementing one or more automated algorithms to determine an updated set of hyperparameters.

The method including presenting, through the user interface, information indicative of a comparison of model prediction and observed outcomes for one or more particular clinical trial subjects. Training one or more other machine learning models using the training data and simulating, using the trained other machine learning models, one or more expected outcomes of a future clinical trial, wherein the relationship between characteristics of clinical data associated with the future clinical trial is similar to the relationship between the characteristics of the stored clinical data associated with one or more clinical trials. The clinical data including clinical trial data, non-clinical trial health data, synthetic clinical trial data, or synthetic non-clinical trial health data.

The method including determining one or more groups of clinical trial subjects with associated clinical data in the data repository, where the clinical trial subjects in each of the one or more groups have common clinical characteristics and clinical outcomes and determining one or more groups of clinical trial subjects with associated clinical data in the data repository, wherein the clinical trial subjects in each of the one or more groups have common clinical characteristics and clinical outcomes. Presenting, through the user interface, one or more interactive graphical representations of the clinical data of the particular clinical trial subject in relation to clinical data of clinical trial subjects in one or more of the groups.

The method including presenting, through the user interface, information indicative of one or both of one or more safety signals and one or more efficacy signals, the information sufficient to terminate the ongoing clinical trial. Presenting, through the user interface, information enabling real-time oversight of the ongoing clinical trial. Presenting, through the user interface, information indicative of whether the particular clinical trial subject of the ongoing clinical trial is an outlier in relation to clinical trial subjects in one or more of the groups of clinical trial subjects. Presenting, through the user interface, information indicative of a comparison of clinical data related to clinical trial subjects of the ongoing clinical trial with clinical data related to one or more clinical trials from the clinical data stored in the data repository. Presenting, through the user interface, information indicative of one or more reviews of raw clinical data, predicted safety signals, and predicted efficacy signals related to one or more clinical trial subjects of the ongoing clinical trial. Presenting, through the user interface, information indicative of one or more groups of clinical trial subjects, each group comprising clinical trial subjects with similar clinical characteristics including demographics, medical history, and treatment outcomes.

The subject matter described in this specification can be implemented in particular embodiments to realize one or more of the following advantages. Techniques are described for implementing a method for detecting signals related to subjects participating in a clinical trial, in which the signals are indicative of one or both of a safety signal and an efficacy signal. A unified data repository that includes clinical data from multiple data sources provides a robust set of training data to train one or more machine learning models on clinical trial data and non-clinical trial health data. By receiving reviews and iterative feedback of the predicted signals through a user interface based on statistical analysis and domain expertise, the corresponding predictions are accurate and sensitive enough to provide recommended actions in relation to a particular clinical trial subject to increase the safety and efficacy of the provided treatment.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 5 is a flow diagram that illustrates an example process for predicting a safety signal and/or an efficacy signal.

FIG. 12 displays an example user interface.

FIG. 14 displays an example comparison of multiple machine learning models that generate an efficacy signal prediction.

FIG. 15 displays an example comparison of multiple machine learning models that generate a safety signal prediction.

Like reference numbers and designations in the various drawings indicate like elements.

DETAILED DESCRIPTION

Figure 1:
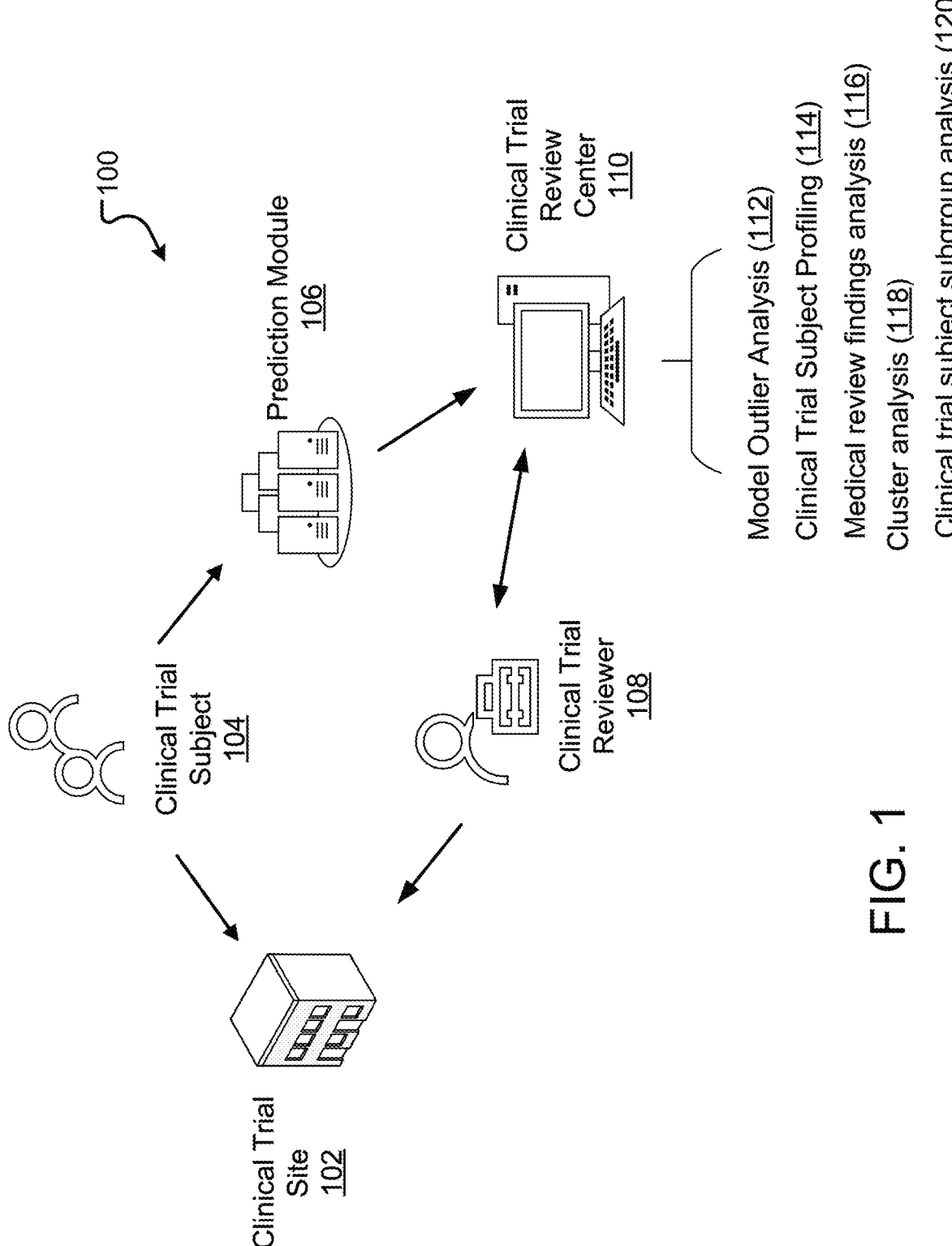
FIG. 1 illustrates an example approach for predicting a safety signal and/or an efficacy signal associated with a subject of a clinical trial.

The systems and techniques described here relate to the early prediction of signals that relate to the safety (e.g., adverse events) and/or efficacy of a treatment for a clinical trial subject associated with a clinical trial. The early prediction of clinical trial signals is important to lead to preemptive measures that enhance the integrity of a clinical trial and the safety of its subjects. Clinical data (e.g., clinical trial data, non-clinical trial health data, synthetic data, standard of care, literature, genomic data, etc.) from multiple sources exist in a variety of formats with a variety of features. By continuously ingesting, standardizing, and storing clinical data from multiple sources in a single data repository with features that include demographics, vitals, medical history, laboratory results and ongoing treatment responses, predictive models coupled with planning and review (e.g., feedback based on domain expertise) can identify reliable and subtle patterns that may precede the occurrence of adverse events and/or may indicate a potential treatment efficacy issue (e.g., ineffective treatment, decline in treatment efficacy, etc.). Operation of these trained models can predict occurrence of such safety/efficacy issues for particular clinical trial subjects. This proactive approach allows for timely intervention, potentially mitigating the severity of the adverse events, enhancing patient safety, and improving the overall integrity of the clinical trial.

The systems and techniques described here include user interfaces that provide access to graphical representations of clinical data for medical professionals and clinical trial administrators to effectively plan and review the configuration of the predictive models to ensure safe and accurate predictions. The user interfaces enable clinical trial administrators to plan multiple aspects of the predictive models. The graphical representations through the user interfaces provide analyses including real world data (e.g., non-clinical trial health data) subgroup identification and optimization, historical clinical trial synthetic data identification and optimization, functionality that enables a review, by a clinical trial administrator or other medical personnel, of the parameters that determine the accuracy and reliability of the predictive models, and access to multiple additional predictive models that can recommend changes to a particular clinical trial protocol, standard of care protocols, and potential necessary changes due to regulatory considerations.

In addition to the one or more user interfaces that enable the planning and configuration of predictive models and governance over the central data repository, clinical trial reviewers can access user interfaces to review predictions, clinical trial subject profiles, group profiles, and initiate actions in response to the predictions. The clinical trial reviewers act independently from the clinical trial administrators, such that clinical trial reviews and associated predictions are unbiased. The independent planning and review stages maintain the integrity of a particular clinical trial, ensuring decisions regarding continuation, modification, or termination of the particular clinical trial are made based on unbiased reviews of the associated clinical data. The user interfaces that enable an unbiased review of clinical trial data include analyses like predictions from multiple predictive models, data mining results from ongoing clinical trial data, model comparisons, clinical trial subject profiles, and functionality for the reviewer to provide feedback that initiates updates to the predictive models or initiates specific actions related to a particular clinical trial or clinical trial subject.

FIG. 1 illustrates an example approach 100 for predicting one or both of a predicted safety signal and a predicted efficacy signal associated with a clinical trial subject 104 that participates in an ongoing clinical trial. During the course of the clinical trial, a clinical trial subject receives care from medical personnel at one or more clinical trial sites (e.g., clinical trial site 102). In some cases, a clinical trial site 102 can host one or more clinical trials, where each clinical trial has one or more clinical trial subjects. In some cases, each clinical trial is managed or overseen by a clinical trial reviewer 108, e.g., one or more individuals or entities responsible for aspects of the clinical trial, such as safety and/or efficacy of the clinical trial. The clinical trial site 102 can be, e.g., a single location like a hospital, clinic, or doctor's office that implements a protocol corresponding to a clinical trial, or a group of related locations implementing the protocol corresponding to the clinical trial and operating under the same administration. In general, a clinical trial protocol defines the treatments, objectives, and other parameters of the clinical trial. In some cases, the clinical trial site 102 collects clinical data associated with the clinical trial subjects that participate in the corresponding clinical trial.

The data collected by the clinical trial site 102 about the participating clinical trial subjects, e.g., the clinical trial subject 104, among others, can be used to train a prediction module 106 to identify patterns in clinical trial data collected from one or more ongoing clinical trials. The prediction module includes one or more trained machine learning models that predict one or both of a predicted safety signal and a predicted efficacy signal associated with specific clinical trial subjects (e.g., the clinical trial subject 104) based on clinical characteristics of the subjects. The prediction model 106 processes clinical characteristics of the clinical trial subject 104, e.g., specifics of the treatment received in relation to the clinical trial, administered medications, adverse events, biomarkers etc. In some implementations, the prediction module 106 determines one or both of a predicted safety signal and a predicted efficacy signal for the clinical trial subject 104 based on these processed clinical characteristics and outputs the prediction(s) to a clinical trial review center 110. In addition, or alternatively, in some implementations, the prediction module 106 outputs one or both of the corresponding predicted safety signal and the predicted efficacy signal directly to the clinical trial reviewer 108.

In general, the one or more machine learning models of the prediction module 106 can be trained using clinical data from multiple clinical trial subjects from multiple clinical trials across many different domains and areas of medicine. The description in relation to FIG. 1 describes the one or more machine learning models trained on clinical trial data from the clinical trial site 102. However, a more general case of the one or more machine learning models trained on clinical data from multiple clinical data sources is possible. In some cases, the clinical data used to train the one or more machine learning models does not include clinical data from the clinical trial subject 104 or the clinical trial site 102.

The predicted safety signal for a given clinical trial subject is indicative of the predicted future safety of the clinical trial treatment provided to the clinical trial subject. For example, the predicted safety signal can indicate a likelihood of an occurrence of an adverse event for the clinical trial subject. In some implementations, the predicted safety signal is an integer of a fixed range of integers. In some other implementations, the predicted safety signal is an integer of an infinite range of integers. In some other implementations, the predicted safety signal is a continuous variable in a finite or infinite range. The one or more machine learning models can output a predicted safety signal that increases as the safety of the clinical trial subject in the clinical trial increases. Alternatively, the machine learning models can output a predicted safety signal that decreases as the safety of the clinical trial subject in the clinical trial increases.

The predicted efficacy signal for a given clinical trial subject is indicative of whether the treatment or intervention of the particular clinical trial subject produces the desired beneficial effect under ideal, controlled conditions. It is an indication of how well a specific treatment or intervention works when study conditions are strictly managed to minimize variability other than the treatment itself. In some cases, the predicted efficacy in relation to one or more clinical trial subjects provides insight into the efficacy of a particular clinical trial. The efficacy of the particular clinical trial is measured by specific outcomes defined in the clinical trial protocol, such as the proportion of clinical trial subjects who achieve a certain level of symptom relief, the reduction in tumor size in cancer patients, or the number of patients who reach a certain biomarker in a trial for a new medication. The range of possible predicted efficacy signal values includes both infinite and finite ranges of integer or continuous variables. In general, the predicted safety signal is indicative of how successful a clinical trial is in relation to its objectives and ideal outcomes according to a corresponding clinical trial protocol.

The clinical trial reviewer 108 can review one or both of the predicted safety signal and predicted efficacy signal from the prediction module 106 through a user interface provided by the clinical trial review center 110. In some implementations, the clinical trial reviewer 108 is responsible for conducting the clinical trial activity associated with one or more clinical trial sites (e.g., the clinical trial site 102) safely and effectively, and can initiate changes in a particular clinical trial protocol or specific activity associated with the particular clinical trial or clinical trial site 102. In addition, the review provided by the clinical trial reviewer 108 can be used to re-train the one or more machine learning models of the prediction module 106 with new training data and/or updated hyperparameters (e.g., parameters that affect the training process), and/or to re-determine one or more predictive features that are processed by the one or more machine learning models.

In some implementations, the prediction module 106 generates a predicted signal that is a combination of a predicted safety signal and a predicted efficacy signal. In this case, the clinical trial reviewer 108 or other personnel associated with the clinical trial can determine a first weight associated with the degree to which the combination reflects the safety of the clinical trial or clinical trial subject and a second weight associated with the degree to which the combination reflects the efficacy of the treatment provided during the clinical trial.

The clinical trial reviewer 108 reviews the predicted signals from the prediction module 106 using a user interface associated with the clinical trial review center 110. The user interface can present one or more interactive graphical representations of the clinical data of the clinical trial subject 104 in relation to model outlier analysis 112, clinical trial subject profiling 114, medical review findings analysis 116, cluster analysis 118, and clinical trial subgroup analysis 120. Further discussion of the details of the graphical representations presented on the user interface is provided in relation to descriptions of the following figures.

The clinical trial reviewer 108 or other medical professionals can review the predicted signals along with additional context related to clinical trial data on the user interface of the clinical trial review center 110. The clinical trial review center 110 provides real-time oversight of clinical trial subjects and clinical trial sites.

In some cases, the clinical trial reviewer 108 can review data related to the predicted safety signal and the predicted efficacy signal through the user interface, where the signals provide information sufficient to enable intervention in care received by the clinical trial subject 104 through the ongoing clinical trial associated with the clinical trial site 102.

Figure 2:
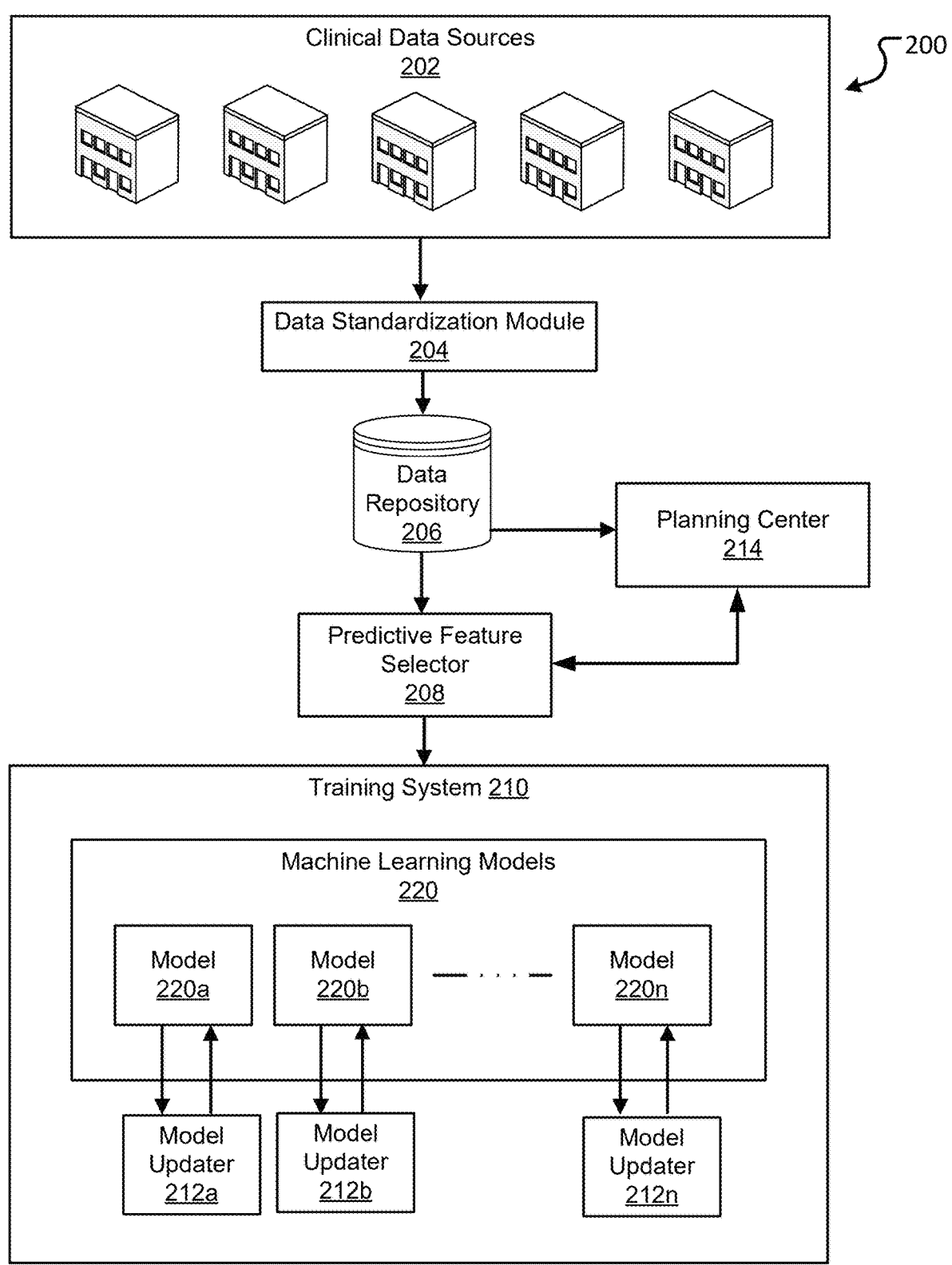
FIG. 2 is a block diagram that illustrates an example of a system that trains one or more machine learning models.

FIG. 2 is a block diagram that illustrates an example of a system 200 that includes a training system 210 to train one or more machine learning models 220 to predict one or both of a signal associated with a degree of safety or a signal associated with a degree of efficacy for a particular subject of a particular clinical trial and the treatment received by the particular clinical trial subject in relation to the particular clinical trial.

The system 200 collects clinical data from one or more clinical trial sources 202. The clinical data can include clinical trial data associated with multiple clinical trial subjects that are participating in multiple clinical trials, such as vital signs, test results, treatment protocols, prescribed medications, treatment outcomes, adverse events, etc. In addition, the clinical data can include non-clinical trial health data from non-clinical trial data sources, e.g., from electronic health records, medical claims, patient surveys, etc. Non-clinical trial health data can be collected by observing treatments and outcomes in the field from primary care physicians, pharmaceutical companies, and/or hospitals. Non-clinical trial health data can be associated with clinical trial participants from healthcare data sources separate from the clinical trial or from non-clinical trial participants. In addition, the clinical data can include synthetic clinical trial data and synthetic non-clinical trial health data that includes data generated by one or more algorithms or processes based on patterns observed in relation to clinical trial data and/or observed non-clinical trial health data.

Clinical data collected from a variety of sources can have different formats, data types, fields, categories, etc. Cleaned and standardized clinical data facilitates training of the one or more machine learning models 220. In addition, the system 200 redacts personally identifiable information about patients before it is analyzed and stored to comply with regulatory frameworks (e.g., Health Insurance Portability and Accountability Act (HIPAA)). A data standardization module 204 processes the clinical data of the one or more clinical data sources 202. In some implementations, the data standardization module 204 collects and standardizes clinical data from a variety of sources including electronic data capture systems, clinical trial management systems, interactive response technology systems, electronic clinical outcome assessments, consent forms, laboratory results, electronic trial master files, and connected devices. The clinical data associated with each source can be acquired through file based SFTP transfers, application programming interfaces, or from streaming sources associated with connected devices. The data standardization module 204 maps each instance of clinical data to a canonicalized form, which enhances downstream predictive accuracy when considering a data repository that includes data from multiple diverse sources in a single unified format. In addition to standardization, the data standardization module 204 de-identifies the clinical data by redacting personally identifiable information from the clinical data.

The data standardization module 204 provides the redacted and standardized clinical data to a data repository 206, where the data repository 206 stores a variety of data in a variety of formats, including the standardized form generated by the data standardization module 204. In some implementations the data repository stores one or more data types including redacted personally identifiable information, raw data, processed data, study specific data, subject specific data, canonical data, queries, issues, AI-generated synthetic data, real-world data, relevant publications, or healthcare ontologies.

A predictive feature selector 208 determines one or more predictive features (e.g., feature selection) from the data stored in the data repository 206 in relation to the clinical data. A predictive feature is a feature of a data set that has predictive value with respect to an output of a predictive process. For example, a predictive feature of the stored clinical data is a characteristic (e.g., a particular variable or combination of variables) that correlates with one or both of an efficacy signal and a safety signal associated with a population of clinical trial subjects. As another example, if a data repository includes human body data corresponding to individuals, e.g., height, weight, foot size, etc., the weight feature of the dataset may have more predictive value of whether an individual is diagnosed with diabetes compared to height. However, height likely has some predictive value since height and weight are often correlated, but less predictive value than weight. In some cases, a predictive feature is determined to be a linear combination of two or more features. For example, a strong predictive feature of this dataset of whether an individual is diagnosed with diabetes can be a linear combination of height and weight with appropriate weighting coefficients for each feature.

The predictive feature selector 208 can perform feature selection using a variety of approaches. For example, the predictive feature selector 208 can implement one or more of t-distributed stochastic neighbor embedding, analysis of variance, principal component analysis, linear discriminant analysis, independent component analysis, hierarchical agglomerative clustering, partitioning around medoids clustering, Gaussian mixture models, or labeling based on signals identified in past relevant studies. In addition, domain expertise can be leveraged as a resource to determine which features of the clinical trial data are most likely to correlate with one or both of a particular safety signal and efficacy signal.

In addition to statistical methods of determining predictive features of the clinical data, a planning center 214 with a user interface can provide one or more individuals, e.g., medical professionals, the opportunity to review data from the data repository 206 and actively participate in the selection of predictive features. For example, the predictive feature selector 208 can implement a statistical process to determine one or more possible candidates for predictive features with a high predictive value and provide the analysis to an individual through the user interface of the planning center 214. The individual can apply domain expertise based on professional experience as well as judgement extracted from direct analysis of the data stored in the data repository 206 to evaluate the automated analysis and provide direction for how to modify the determined predictive features.

The predictive feature selector 208, using one or more statistical methods and/or domain expertise facilitated by the user interface of the planning center 214, determines which fields of the standardized clinical trial data that is stored in the data repository 206 are most likely to provide an accurate prediction of one or both of a safety signal and efficacy signal corresponding to a particular clinical trial subject. In some implementations, the predictive features can be determined to accurately predict additional or alternative signals or outcomes that correspond to features of the data stored in the data repository 206.

One or more machine learning models 220 are trained, using clinical data stored in the data repository 206, to predict a safety signal and/or efficacy signal related to a particular clinical trial subject. The training system 210 processes multiple training data items and iteratively modifies parameters of one or more machine learning models 220 to minimize an error between the predicted outcomes and the observed outcomes associated with the data in the data repository 206. For each training data item, the training system 210 receives clinical data stored in the data repository 206 corresponding to a particular clinical trial subject and an indicator of one or both of a safety signal and an efficacy signal associated with the clinical trial subject. The training system 210 receives multiple training data items, each training data item corresponding to a training run. In some implementations, the training system 210 receives training data items in batches and trains the machine learning models 220 accordingly with the batches of training data items. In some implementations, the training system 210 receives more than one batch of training data items corresponding to non-overlapping subsets of clinical data to train a subset of one or more machine learning models 220. In some implementations, each training data item includes one or more predictive features derived from a clinical data item stored in the data repository 206 and generated by the predictive feature selector 208, e.g., a predictor, and an indicator of one or more associated signals, e.g., a label.

The training system 210 processes the one or more predictive features extracted by the predictive feature selector 208 with each of the machine learning models 220. The system 200 configures each of the N machine learning models 220 as a particular type of machine learning model. For example, the system 200 can configure model 220a as a distributed random forest machine learning model, model 220b as an artificial neural network, and model 220n as a generalized linear model. Each type of machine learning model 220 has a corresponding architecture, training method, set of parameter types, and sets of hyperparameters that differ from each other machine learning model 220.

In some implementations, the system 200 configures one or more machine learning model of the machine learning models 220 to employ unique machine learning architectures (e.g., neural network, support vector machine, or random forest) and trains each machine learning model on a common set of clinical trial data.

In some other implementations, the machine learning models 220 include a single machine learning model.

In some other implementations, the system 200 trains a first subset of the machine learning models 220 on a first subset of clinical data and trains a second subset of the machine learning models 220 on a second subset of the clinical trial data. The system 200 can configure each machine learning model (e.g., model 220a-n) to be trained on any appropriate subset of the clinical data and configured to execute computations according to any machine learning architecture.

In some other implementations, the system 200 configures one or more machine learning models to employ the same machine learning architecture with varying hyperparameters (e.g., learning rate, number of layers, initialization parameters, training threshold, number of iterations).

In some other implementations, the system 200 can train one or more machine learning models that employ the same machine learning architecture with different subsets of the clinical data.

The system 200 can configure any subset of the machine learning models 220 to employ any combination of machine learning architectures, with any combination of configuration hyperparameters, on any subset of the clinical data.

To train the N machine learning models 220, the training system 210 receives training data items from the predictive feature selector 208 to iteratively determine the parameters of each of the N machine learning models 220. Each training data item processed by the training system 210 constitutes a training run for each of the N machine learning models 220. In some implementations, each machine learning model of the N machine learning models 220 is trained independently. In other words, the training system 210 determines parameters that define each of the machine learning models independently using the same set of training data items delivered to the training system 210 by the predictive feature selector 208. The structure and training process of each machine learning model can be unique relative to the other machine learning models. In some other implementations, one or more of the N machine learning models are coupled. For example, parameters of a first machine learning model (e.g., model 220a) are initialized based on parameters of a trained second machine learning model (e.g., model 220b).

In some implementations the predictive feature selector 208 selects different predictive features of the clinical data for one or more machine learning models 220. In some cases, a particular architecture or configuration of a first machine learning model generates more accurate predictions compared to a second machine learning model with a different architecture or configuration. In some implementations, the predictive feature selector 208 selects different predictive features of the clinical data for different subsets of the clinical data.

For each training run corresponding to a training data item, the training system 220 evaluates each machine learning model (e.g., machine learning model 220a-n) of the N machine learning models 220 to generate corresponding outputs. Each output describes one or both of a predicted safety signal and a predicted efficacy signal associated with a particular clinical trial subject corresponding to the training data item.

For a particular training data item, a corresponding model updater processes the output generated by each of the N machine learning models 220. For example, a model updater 212a processes an output from machine learning model 220a. The model updater 212a determines a difference between the output of machine learning model 220a and the label, e.g., the indicator of one or more associated safety and/or efficacy signals, as represented in the data stored in the data repository 206.

In some implementations, the difference between the output of machine learning model 220a and the label is characterized by a mean square error between the output and the label. The model updater 212a implements an iterative algorithm (e.g., gradient descent or similar) to adjust the weights of machine learning model 220a in an attempt to reduce the difference for a subsequent training run.

When the difference decreases below a pre-defined threshold, the training system 210 stops processing training data items and the parameters that define each of the N machine learning models 220 (e.g., machine learning model 220a) are considered to be determined. In some cases, the learning rates vary between one or more of the N machine learning models 220. In this case, the training system 210 continues to train a subset of the N machine learning models 220, as each machine learning model can have unique training parameters such as learning rates and learning thresholds.

Figure 3:
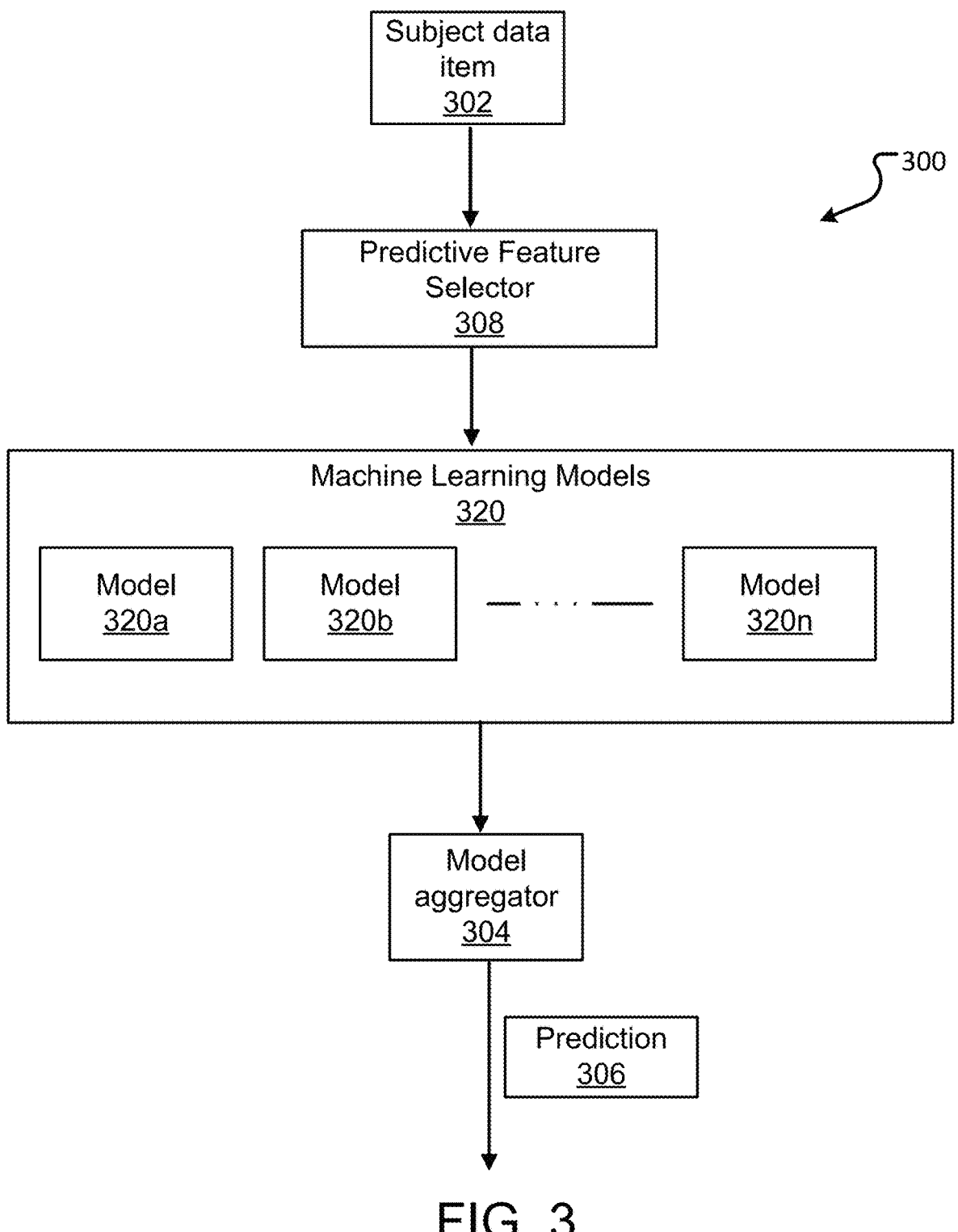
FIG. 3 is a block diagram that illustrates an example of a system that predicts a safety signal and/or an efficacy signal.

FIG. 3 is a block diagram that illustrates an example of a system that predicts one or both of a safety signal and an efficacy signal associated with a subject of a clinical trial based on predictive features associated with the subject. One or more trained machine learning models 320 process a subject data item 302 to generate one or more associated outputs. The subject data item 302 includes clinical data related to a particular clinical trial subject. The particular clinical trial subject may or may not have associated clinical trial data represented in the clinical trial data repository (e.g., the clinical trial data stored in the data repository 206). In some cases, the clinical trial data associated with the clinical trial subject is new data and is not represented in the clinical trial data stored in the data repository and used to train the one or more trained machine learning models 320. For example, the subject data item 302 can correspond to a clinical trial subject that participates in an ongoing clinical trial.

In some implementations, the subject data item 302 characterizes the medical history of the clinical trial subject and characteristics of activities of the clinical trial subject related to a particular clinical trial. In some cases, the corresponding clinical trial data include laboratory results, vital measurements, electrocardiogram (ECG) measurements, concomitant medications (CONMEDs), and occurrences of adverse events.

A predictive feature selector 308 determines one or more predictive features from the subject data item 302. The predictive features are the same predictive features used by the corresponding predictive features selector 208 in relation to the training system 210. The selection of predictive features is performed during the process of training the one or more machine learning models 220. The trained machine learning models 320 have a corresponding set of predictive features that were used to train the models, and the predictive feature selector 308 implements the same approach to extracting a particular set of predictive features from a subject data item 302 as the training process. For example, if the training system 210 trained the one or more machine learning models 220 on a set of predictive features that included a linear combination of electrocardiogram data and occurrences of specific adverse events, the predictive feature selector 308 selects the same linear combination of features from the subject data item 302 during the inference step to be processed by the one or more trained machine learning models 320.

Each of the one or more trained machine learning models 320 processes the predictive features, or a subset of the predictive features determined by the predictive feature selector 308 to generate an independent evaluation of one or both of a predicted safety signal and a predicted efficacy signal. For example, each of the models 320a-n process the predictive features independently to generate a corresponding output that can be interpreted as a predicted signal. In some implementations, the outputs of one or more trained machine learning models 320 are not independent. In other words, the output of a first machine learning model (e.g., model 320a) affects the output of a second machine learning model (e.g., model 320b). In some implementations, the output of one or more machine learning model is a parameter that is further processed to be interpreted as a predicted safety signal and/or predicted efficacy signal, where the parameter is considered to be correlated with the predicted signal.

In some implementations, a model aggregator 304 aggregates the outputs of the trained machine learning models 320 to determine a single prediction 306 of one or both of a predicted safety signal and a predicted efficacy signal. The model aggregator 304 can combine the outputs from one or more trained machine learning models 320 using a linear combination with associated weights, or any other function that combines one or more outputs from the one or more trained machine learning models 320 into a single prediction 306. In some cases, the model aggregator 304 can generate a probability distribution of predicted signals.

In some implementations, the model aggregator 304 determines a prediction 306 associated with a prediction of one or both of a safety signal and an efficacy signal by considering each of the outputs generated from each of the machine learning models 320. For example, the model aggregator 304 can determine the prediction 306 as the mean, median, or mode probability across all of the outputs of the machine learning models 320. As another example, the model aggregator 304 can determine the prediction 306 as the predicted safety signal and/or predicted efficacy signal that is shared by the highest percentage of outputs from the machine learning models 320 (e.g., if 80% of the predicted signal from the machine learning models 320 is 60±10%, the model aggregator 304 can determine 60±10% to be the prediction 306).

Figure 4:
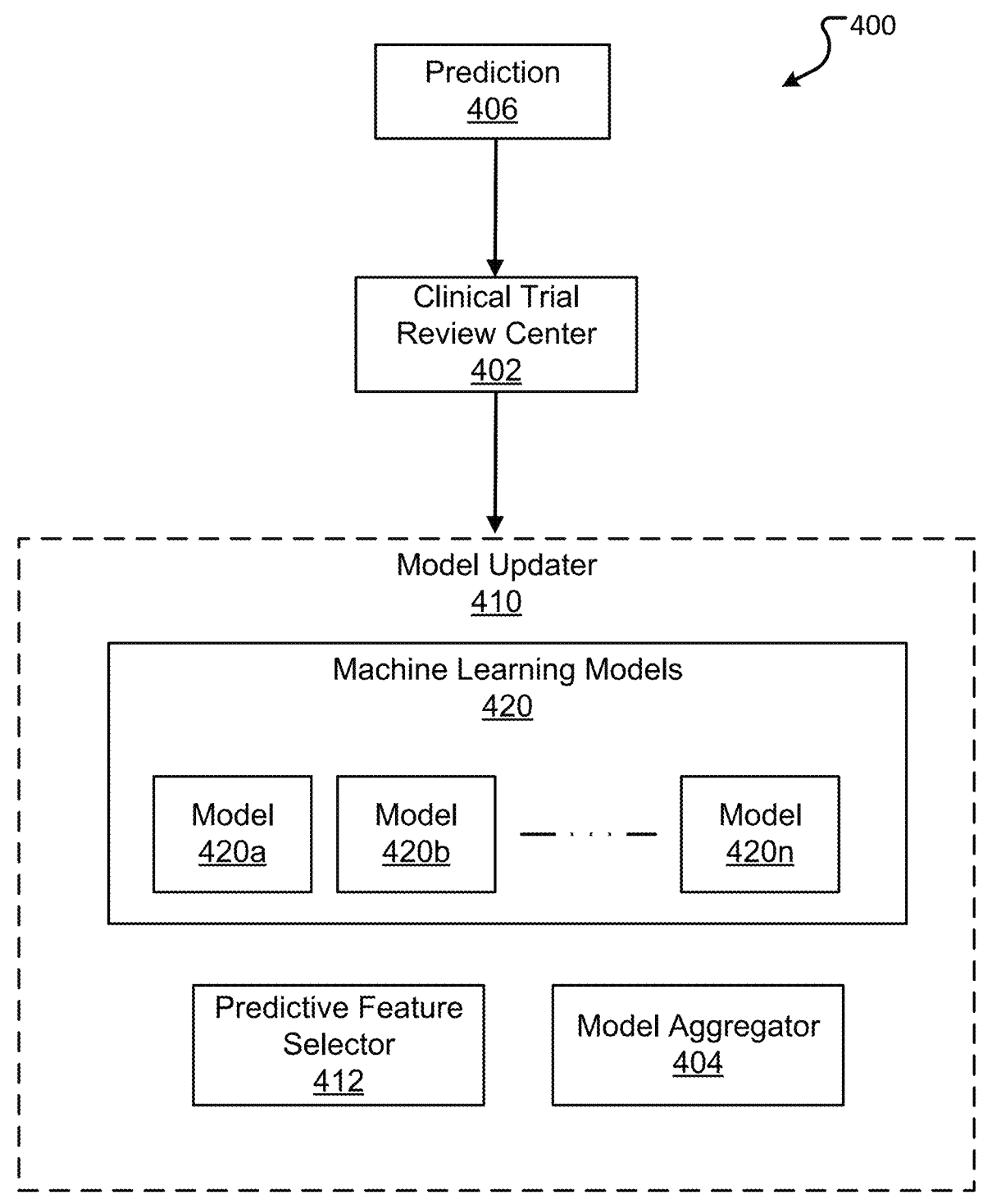
FIG. 4 is a block diagram that illustrates an example of a system that updates one or more machine learning models and/or predictive features.

FIG. 4 is a block diagram that illustrates an example of a system 400 that updates one or more trained machine learning models 420 and/or predictive features 412 based on a review of a prediction 406 that is facilitated by a user interface of a clinical trial review center 402.

As described in relation to FIG. 2, a training system 210 trains one or more machine learning models 220 and receives predictive features as determined by a predictive feature selector 208. The training system 210 determines a set of parameters for each machine learning model and the predictive feature selector 208 determines a set of one or more predictive features that serve as the inputs for each respective machine learning model 220. The result of a process performed by the system described in relation to FIG. 2 is a set of one or more trained machine learning models 420 and a predictive feature selector 412 that determines a set of one or more predictive features of an input subject data item (e.g., subject data item 302 that corresponds to a particular set of clinical data associated with a particular clinical trial subject). The predictive feature selector 402 implements both automated feature selection techniques and feedback based on domain expertise captured by the user interface of the planning center 214.

As a particular clinical trial progresses over time, clinical data is collected about the clinical trial subjects associated with it. A prediction module, e.g., the one or more trained machine learning models 320, generates predictions (e.g., prediction 406) of one or both of a safety signal and an efficacy signal associated with a clinical trial subject, a clinical trial reviewer (e.g., a medical professional) reviews the signals and associated clinical data to determine if the predicted signal(s) are valid and medically reasonable based on the domain expertise of the reviewer. The clinical trial reviewer can review the predicted signals periodically at a fixed time interval, as new predicted signals are made available, or based on any schedule that is appropriate for the scope and objectives of the particular clinical trial. The clinical trial reviewer reviews the one or more predictions along with associated clinical data through a user interface of the clinical trial review center 402.

In some implementations, the clinical trial reviewer indicates a positive or negative review in relation to the prediction 406 which is indicative of whether the clinical trial reviewer considers the prediction 406 to be a valid signal. In some cases, the review includes text, audio, or video comments that explain particular nuance around the positive or negative review. In some cases, the clinical trial reviewer provides references, details, and other supporting information to support the provided review through the user interface of the clinical trial review center 402.

The review provided by the clinical trial reviewer through the user interface of the clinical trial review center 402 is provided to a model updater 410. The model updater 410 can update the one or more trained machine learning models 420 (e.g., the models 420*a-n*) and update the predictive feature selector 412.

As a particular clinical trial progresses over time and the predictions of the one or more trained machine learning models 420 are evaluated by medical professionals or other automated systems to evaluate accuracy, the model updater 410 can update the learned parameters of the one or more trained machine learning models 420, the strategy implemented by the predictive feature selector 412, and a model aggregator 404. The model updater 410 can update the model parameters, predictive features, and model aggregation to increase the accuracy of the predictions made by the system.

As an example of how the model updater 410 updates the one or more machine learning models 420, the model updater 410 can re-training one or more machine learning models 420 with updated training data and/or modified training hyperparameters. For example, the review provided by the clinical trial reviewer through the clinical trial review center 402 can be considered a new label which represents a new training data item. In some implementations, the model updater 410 can update the machine learning models 420 periodically (e.g., every day, week, month, etc.) or after a number of reviews of predicted signals are received by the clinical trial review center 402. As another example, the review provided by the clinical trial reviewer through the clinical trial review center 402 can indicate one or more suggestions for how to modify the hyperparameters that define how the one or more machine learning models 420 are trained by a training system (e.g., the training system 210). Hyperparameters include number of training runs, training threshold, and architecture of the models that make up the one or more machine learning models 420. As another example, the review provided by the clinical trial reviewer can include a numerical quantification and rank order of the strength of the predicted signal associated with a particular clinical trial subject to convey a relative prioritization of the signal relative to other predicted signals associated with other clinical trial subjects or relative to the particular clinical trial subject at multiple points in time.

In some implementations, the modification of hyperparameters is performed using an automated approach. Automated approaches for modifying hyperparameters include grid search, random search, Bayesian optimization, gradient-based optimization, or any other technique that determines (e.g., tunes) the training parameters of the one or more machine learning models 420 to increase the accuracy of the outputs.

As an example of how the model updater 410 updates the model aggregator 404, the model updater 410 can update the relative weights that the model aggregator 404 uses to combine the outputs of the one or more machine learning models 420. For example, the review of the prediction 406 can indicate a first subset of models (e.g., model 420*a*) is more accurate than a second subset of models (e.g., model 420*b*). The relative weight of the outputs of the machine learning models 420 (e.g., the weights used by the model aggregator 404 to combine the outputs of the one or more machine learning models 420*a*-420*n* to generate a prediction, e.g., the prediction 306). In some implementations, the clinical trial reviewer can review the outputs of each machine learning model through the user interface of the clinical trial review center 402 to determine which machine learning models produce the most accurate predictions.

As an example of how the model updater 410 updates the predictive feature selector 412, the feature selection procedure described in relation to FIG. 2 can be repeated, in which a user interface of a planning center (e.g., the planning center 214) facilitates a combination of statistical techniques and domain expertise to re-determine one or more, or a combination of, predictive features of the clinical data stored in the data repository (e.g., 206) that are considered to be predictive features of one or both of a safety signal and an efficacy signal. In addition, the model updater 410 can re-determine the relative importance of each predictive feature according to the review. For example, if the review indicates a first predictive feature provides more predictive ability compared to a second predictive feature based on the domain expertise of the clinical trial reviewer, the model updater can adjust the relative importance of the two predictive features accordingly.

As new authoritative and confirmed data is collected through the clinical trial review center, the model updater 410 can update the trained machine learning models 420, the predictive feature selector 412, and the model aggregator 404 to increase the accuracy of the predictions generated by the system.

FIG. 5 is a flow diagram that illustrates an example process 500 for predicting one or both of a safety signal and an efficacy signal associated with a subject of a clinical trial. The process 500 can be performed by one or more systems as described in relation to FIGS. 2-4. For convenience, the process 500 is described as being performed by a system that includes the functionality of the respective systems described in FIGS. 2-4.

The system collects (502) clinical data for patients from multiple sources. The sources include data from electronic data capture (EDC) systems, clinical trial management systems (CTMS), laboratory results (e.g., blood tests), interactive response technology (IRT) systems, electronic clinical outcome assessments (eCOA), consent forms, electronic trial master files (eTMF), connected devices, file-based study transfers from associated contract research organizations (CRO) partners, and other upstream systems that may be associated with specific clinical trials.

In addition to clinical trial data, the clinical data can include non-clinical trial health data (e.g., real-world data) and synthetic data. Non-clinical trial health data is data corresponding to treatment and events that occur outside of the context of a clinical trial. In some cases, non-clinical trial health data is reported by physicians, hospitals, and other medical personnel during routine care of individuals. Synthetic data includes data that is artificially generated based on either non-clinical trial health data or clinical trial data. For example, a machine learning model can be trained to identify patterns in data corresponding to real patients to simulate new data entries that correspond to fictional individuals.

The system standardizes (504) the clinical data from the multiple sources in a common format and redacts personally identifiable information from the clinical data. A data repository stores the clinical data collected (e.g., 502) from the multiple sources. In order to use the clinical data from multiple sources for machine learning and data analysis, the clinical data is standardized, cleaned, and appropriately redacted.

The standardization process can include imputing missing data, e.g., replacing missing categorical data with mode category with respect to the full set or related subset of clinical data. The process can include replacing missing numerical values with a single value such as the mean or median of the value with respect to the full set or related subset of clinical data. In addition, the process can include rebalancing data, e.g., adjusting the clinical data such that all categories are equally represented by over sampling minority categories or under sampling majority categories. In addition, the process can include data harmonization, e.g., aligning data formats, units of measurement, and scales from the multiple sources of clinical data. As an additional example, the process can include data cleaning, e.g., identifying, and correcting inaccuracies, duplicates, etc. As an additional example, the process can include dimensionality reduction which reduces the number of variables of the clinical data to avoid overfitting and high computational costs during machine learning processes. The process can include tokenization, information extraction, and ontology mapping for unstructured data sources.

The system stores (506) the standardized and redacted clinical data in a data repository. The data repository can include one or more data servers and databases. In some implementations, the data repository is a data lake that includes multiple types of data like the standardized data, raw data, relevant documents, publications, and redacted electronic health records.

The system determines (508) one or more predictive features, wherein each predictive feature corresponds to one or more characteristics (e.g., biomarkers) of the stored clinical data that correlate with one or both of an efficacy signal and a safety signal for the patients. The process of determining one or more predictive features includes transforming the clinical data to increase the predictive performance of the one or more machine learning models.

The system determines the predictive features using one or more processes that include a combination of domain expertise, exploratory analysis, and statistical methods. For example, a literature review of published studies, guidelines, and treatment protocols can identify potential safety signals and efficacy signals. As another example, consultation with experts in a relevant field can provide additional insights into the current standard of care and potential safety signals. As another example, non-clinical trial health data analysis can help a medical professional identify patterns in disease management and treatment outcomes. The identified patterns can help generate hypotheses about the safety and efficacy of an intervention being studied and inform the design of a protocol of a clinical study and determine which features of the clinical data are predictive of the predicted signals. As another example, adverse event reporting associated with previous clinical trials can reveal potential safety signals that can help generate hypotheses about the safety of the particular intervention in a particular patient population. The aforementioned sources of data that originate from outside a particular clinical trial combined with domain expertise contribute to the determination of one or more predictive features of the clinical data.

In addition to statistical methods and domain expertise, the system can transform the clinical data to facilitate the determination of predictive features. For example, numeric aggregations of numerical features (e.g., height, weight, age, etc.) such as the mean, standard deviation, count, etc., for longitudinal data (e.g., data that is evaluated multiple times) can simplify the clinical data to improve the predictive ability of a particular machine learning model. Similarly, numeric scaling of numerical features in which numeric features are transformed into a finite range, e.g., from 0-1, can improve the predictive ability of the feature.

Domain-specific approaches to determining predictive features can improve the predictive ability of machine learning models for a particular domain. For example, an indicator variable that is indicative of whether a clinical trial subject responds to a particular treatment or not can provide domain-specific context to a set of clinical data.

The system obtains (510), from the stored clinical data, training data including one or more predictive features and associated efficacy signal or safety signal. A machine learning model transforms input data into an output value, in which the output volume can be a range of numerical values, a categorical index, or any other type of value. In some implementations, the machine learning can include one or more neural networks or decision trees. The machine learning model iteratively processes training data from the stored clinical data and determines and updates a set of parameters with each training data item based on an error function that evaluates the difference between the output of the machine learning model and a target output. In this case, the target output is one, both, or a combination of a safety signal and an efficacy signal.

The predictive features, as determined (508) from the clinical data using one or more of multiple techniques, are calculated for each training data item and processed by a machine learning model as an input data item.

The system uses (512) the training data to train one or more machine learning models to predict one or both of a predicted efficacy signal and a predicted safety signal for a clinical trial subject based on clinical data for the clinical trial subject. As described in relation to FIG. 2, a training system (e.g., the training system 210) can train one or more machine learning models (e.g., machine learning models 220) with training data extracted from clinical data stored in a data repository (e.g., data repository 206) and processed by a predictive feature selector (e.g., predictive feature selector 208).

The system receives (514) clinical data for a particular clinical trial subject enrolled in an ongoing clinical trial. With one or more trained machine learning models (corresponding to the one or more machine learning models trained in step 512), the system receives clinical data associated with the particular clinical trial subject of the ongoing clinical trial. In some cases, the particular clinical trial subject does not have representative data in the training data, e.g., in the data repository. However, in some cases, the particular clinical trial subject has similar features (e.g., predictive features) as clinical trial subjects represented in the standardized and redacted clinical data.

By the trained machine learning models, the system predicts (516) one or both of a particular efficacy signal and a particular safety signal for the particular clinical trial subject based on one or more predictive features determined from the received clinical data for the particular clinical trial subject. As described in relation to FIG. 3, the one or more machine learning models (e.g., machine learning models 320) process an output of a predictive feature selector (e.g., predictive feature selector 308) to generate a prediction (e.g., prediction 306).

The system receives (518), through a user interface, a review of the particular efficacy signals, safety signal, or both. As described in relation to FIG. 4, a clinical trial review center with a corresponding user interface provides one or more graphical representations of the clinical data and the predictions associated with one or more clinical trial subjects.

The system updates (520) the one or more trained machine learning models based on the review, including one or more of (i) re-training one or more of the trained machine learning models using updated training data, (ii) re-determining one or more of the predictive features based on the review, or (iii) re-training one or more of the trained machine learning models with an updated set of corresponding hyperparameters. As described in relation to FIG. 4, a model updater can modify one or more machine learning models by re-training the models with updated hyperparameters or new hyperparameters. In addition, the model updater can update the predictive features identified by a predictive feature selector based on the review from a clinical trial reviewer.

Figure 6:
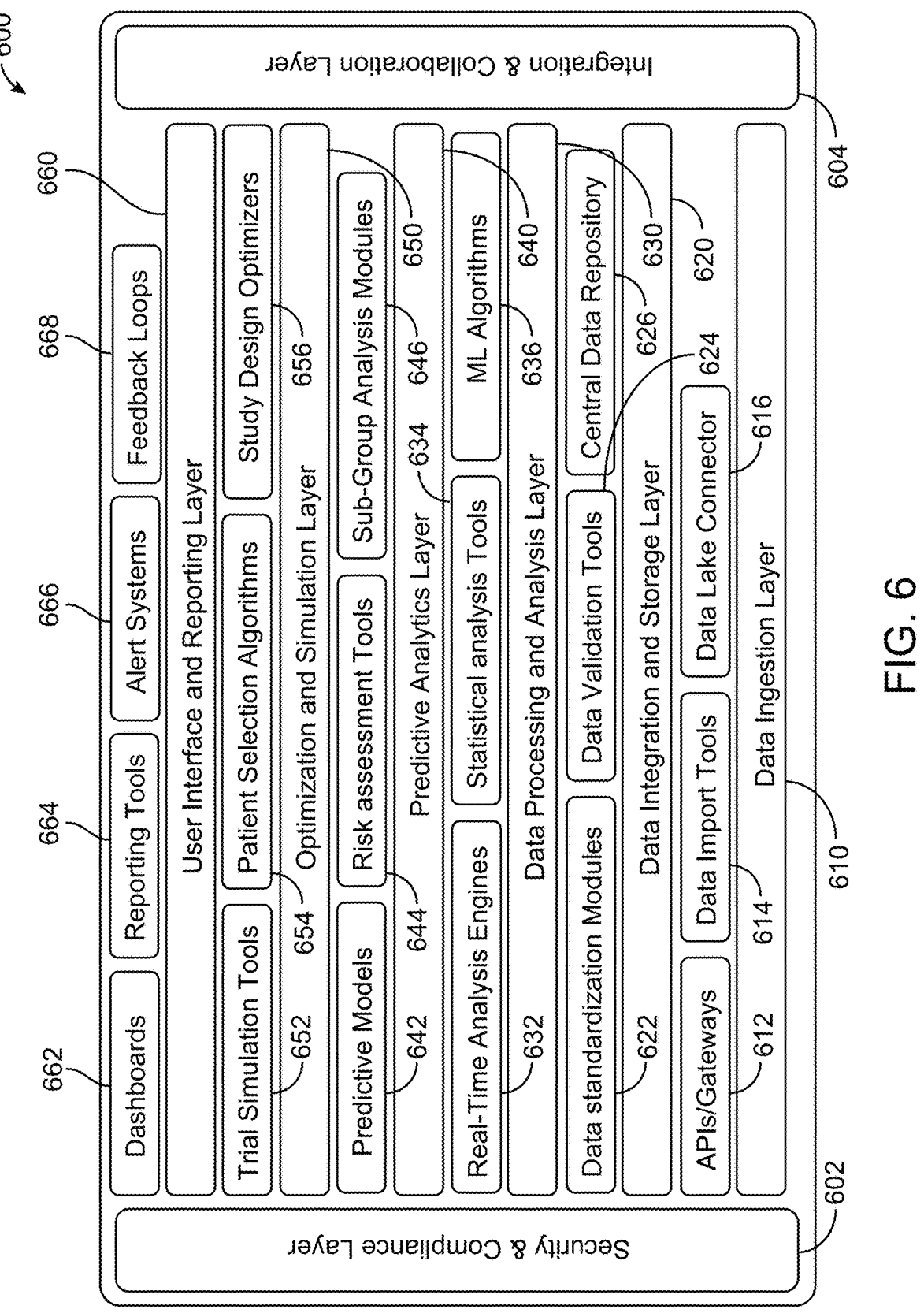
FIG. 6 illustrates an example system for ingesting and analyzing clinical data.

FIG. 6 illustrates multiple components of a system 600 that performs clinical data ingestion and processing to predict one or more signals related to a clinical trial and/or clinical trial subject. The components of the system 600 are described in relation to FIG. 1-5. The illustration shown in FIG. 6 depicts an approach for ingesting and processing clinical data in which one or more components of the system 600 are implemented using one or more computers and/or user interfaces.

The system 600 includes multiple data layers. Each data layer transforms clinical data using one or more algorithms and/or manual data manipulation techniques. A security and compliance layer 602 manages security and compliance considerations across each of the data layers of the system 600. For example, the security and compliance layer 602 manages access controls, determining which individuals and roles have access to clinical data, user interfaces, reports, and related insights corresponding to each data layer. In addition, the security and compliance layer 602 manages compliance with one or more regulatory frameworks which may require specific data storage techniques, redaction of personally identifiable information, and necessary consent from clinical trial subjects and/or medical professionals.

An integration and collaboration layer 604 manages oversight over the processes and access to the data related to actions performed by the data layers through one or more user interfaces and/or application programming interfaces (APIs) with external monitoring and reporting systems.

A data ingestion layer 610 collects clinical data from multiple clinical data sources. Clinical data sources include clinical trial data, non-clinical trial health data (e.g., real-world data), synthetic data, etc. The data ingestion layer 610 includes one or more APIs and gateways 612 (e.g., server endpoints that provide access to one or more data sources), data import tools 614 (e.g., sFTP tools, clinical trial protocol digitization, and image-to-text transformations using artificial intelligence and/or optical character recognition algorithms), and data lake connectors 616. A particular data lake connector can be used to load data collected from various clinical data sources into a unified data lake. In addition, the data lake connector can extract clinical data from on or more available data lakes.

A data integration and storage layer 620 processes the clinical data ingested by the data ingestion layer 610. The data integration and storage layer 620 includes a data standardization module 622, one or more data validation tools 624, and a central data repository 626.

The data standardization module 622 performs data operations as described in relation to the data standardization module 204 of FIG. 2. For example, the data standardization module 622 maps each instance of clinical data collected by the data ingestion layer 610 to a common data format, where multiple entries in at least one database of the central data repository 626 includes data from multiple sources of clinical data represented by a unified data format. In addition, in some implementations, the data standardization module 622 performs smart medical coding, named entity recognition, and document translation.

The data validation tools 624 process the clinical data to address missing data and to clean data to remove inaccurate data. In some implementations, the data validation tools 624 perform subject deduplication and subject data analysis. In some cases, one or more data validation tools 624 are implemented as a user interface. For example, a user interface with a spreadsheet view of a subset of the clinical data in the central data repository 626 provides a convenient method for reviewing possible missing or inaccurate data. In addition, one or more data validation tools 624 can automatically check for missing data, flag potential errors, and set data types (e.g., binary, categorical, continuous, time-to-event, etc.). Data validation tools 624 implemented through a user interface allows a user (e.g., a clinical trial reviewer or medical professional) to reload data to the central data repository 626 after making corrections to a source data file.

In some implementations, the central data repository 626 includes at least one database that includes data from multiple clinical data sources in a common format. In some implementations, the central data repository 626 includes one or more databases of raw clinical data from the multiple clinical data sources. A review of the central data repository 626 through one or more user interfaces can provide a user (e.g., a clinical trial reviewer or a medical professional) to modify one or more fields of the repository. For example, a user can switch a data type from binary to categorical. In some implementations, a user can view a distribution of a particular variable across clinical trial subjects of one or more clinical trials. In addition, in some implementations, through the use of a user interface, a user can assign a particular variable as type of variable that is useful for training a machine learning model. For example, a user can assign a particular variable to be an outcome, a treatment, or a particular biomarker. In some implementations, the user interface can facilitate error checks of clinical data stored in the central data repository 626 to prevent incorrect type designations and duplicate variable assignments.

A data processing and analytics layer 630 processes data stored in the central data repository 626. The data processing and analytics layer 630 includes one or more real-time analysis engines 632, one or more statistical analysis tools 634, and one or more tools to manage and configure one or more machine learning algorithms 636.

The one or more real-time analysis engines 632 and the one or more statistical analysis tools 624 can provide distributions of data stored in the central data repository 626 as clinical data is collected from one or more clinical trial sites and is stored in the repository. The real-time analysis engines 626 can provide insights that can change over a particular time period. For example, a particular real-time analysis engine can perform document quality assurance to ensure ingested documents meet regulatory standards and established standards of quality.

The one or more statistical analysis tools 624 can be used, in some implementations through a user interface, to identify significant associations between one or more variables of the clinical data and patterns (e.g., trends). In some implementations, statistical analysis techniques such as clustering and association rule mining are viewed through a graphical user interface. In some implementations, the statistical analysis tools 624 can be implemented as code through a large language model chatbot, a SQL command line, or a Python script.

The one or more tools to manage and configure machine learning models 636 provide a user, through a user interface, the ability to adjust the predictions of the models. For example, a user can adjust the relative importance of one or more machine learning models to an output associated with a particular prediction (e.g., a safety and/or efficacy signal). As another example, a user can adjust one or more hyperparameters of one or more machine learning models to modify the training procedure of the models (e.g., number of training runs, learning thresholds, etc.). As another example, a user can adjust the variables of one or more predictive features that are processed by the machine learning models to improve the accuracy of the models based on domain expertise of the user. In some implementations, the user can compare the predictions made by the one or more machine learning models, the variables that most influence the predictions, and a comparison of predicted outcomes/signals and observed outcomes/signals.

The predictive analytics layer 640 processes data stored in the central repository 626 and statistical evaluations from the data processing and analysis layer 630 (e.g., averages, variances, clusters, etc.) to provide predictions of healthcare-related outcomes like safety signals and/or efficacy signal of a particular clinical trial subject. In some implementations, the predictive analytics layer 640 includes one or more predictive models 642, one or more risk assessment tools 644, and one or more sub-group analysis modules 646.

The one or more predictive models 642 can provide signals indicative of the safety of a clinical trial subject and/or the efficacy of the treatment in relation to the clinical trial subject, as described in relation to previous figures. In some implementations, the predictive models 642 include a trained machine learning model to predict a next best action. In some cases, the next best action is based on a particular safety signal and/or efficacy signal. For example, if a particular safety signal associated with a particular clinical trial subject indicates the particular subject is at risk, the next best action may be predicted to be a removal of the particular subject from the clinical trial. In addition, in some implementations, the predictive models 642 include a standard operating procedure (SOP) quality assurance (QA) prediction, in which SOPs related to a particular clinical trial are evaluated to ensure they are followed correctly, effective, and achieving the intended outcomes.

The one or more risk assessment tools 644 can provide a user, through a user interface, a prediction of a likelihood of an occurrence of an adverse event (e.g., through a safety signal). In addition, the risk assessment tools 644 can display pharmacodynamics predictions indicative of how a particular treatment or drug interacts with a clinical trial subject, the response of a clinical trial subject to a particular drug based on various factors like the dose, the rate of drug absorption. and particular biomarkers. In some implementations, pharmacodynamics predictions are represented by an efficacy signal. In addition, the one or more risk assessment tools 644 can include a site risk analysis, in which a predictive model predicts a particular risk score or risk score trend related to a particular clinical trial site.

The one or more sub-group analysis modules 646 can identify predictive features in a group of multiple clinical trial subjects with stronger outcomes. For example, within a single clinical trial, a first predictive feature may be strongly correlated with a high safety signal among a first sub-group of clinical trial subjects and weakly correlated with a high safety signal among a second sub-group of clinical trial subjects. However, a second predictive feature may be strongly correlated with a high safety signal among the second sub-group of clinical trial subjects. An analysis displayed, through a user interface, to a user that provides information about predictive features for one or more sub-groups can help fine-tune the inputs to the one or more machine learning models to generate more accurate safety and efficacy signal predictions.

The optimization and simulation layer 650 provides a user, through a user interface, an ability to simulate potential outcomes of a future or ongoing clinical trial, select one or more clinical trial subjects (e.g., patients) based on one or more features, and optimize the design of ongoing and future clinical trial protocols. In some implementations, the optimization and simulation layer 650 includes one or more trial simulation tools 652, one or more patient selection algorithms 654, and one or more study design optimizers 656.

In some implementations, the one or more trial simulation tools 652 provides a user to select a subset of clinical data from the central data repository 226 (e.g., clinical data related to multiple clinical trial subjects and individuals that receive treatment and provide health data outside of clinical trials). In some implementations, trial simulation tools 652 include on or more trained machine learning models that predict an outcome of a clinical trial based on particular characteristics like number of clinical trial subjects, demographics, treatment type, disease type, specific aspects of the clinical trial protocol, etc. In some implementations, the user, through a user interface, can input one or more characteristics of a future clinical trial. One or more machine learning models of the one or more trial simulation tools 652 process the characteristics of the future clinical trial and output a predicted outcome.

In some implementations, the one or more patient selection algorithms 654 assist a user, through a user interface, identify one or more clinical trial subjects (e.g., patients) based on one or more characteristics.

In some implementations, the one or more study design optimizers 654 include one or more trained machine learning models that are trained on characteristics of past clinical trials and associated outcomes (e.g., observed safety outcomes and observed efficacy outcomes). The models can identify patterns and identify improvements for an ongoing or future clinical trial to reduce a probability of an occurrence of an adverse event (e.g., avoid a particular medication or treatment or identify similar clinical trials with observed adverse events).

The user interface and reporting layer 660 provides a user, through a user interface, an ability to monitor clinical trial activity, generate reports, alert clinical trial administrators and/or medical personnel, and improve the one or more machine learning models described in relation to the previous layers of the system 600. In some implementations, the user interface and reporting layer 660 includes one or more dashboards 662, one or more reporting tools 664, one or more alert systems 666, and one or more feedback loops 668.

In some implementations, the one or more dashboards 662, e.g., graphical representations of data through a user interface, provide a user access to view and edit clinical data, analyses of clinical data, and control over the analyses of the clinical data. For example, the one or more dashboards 662 include the clinical trial review center 110 as described in relation to FIG. 1 and the planning center 214 as described in relation to FIG. 2.

In some implementations, the one or more reporting tools 664 provide a user, through a user interface, an ability to generate a report that describes features of a particular clinical trial, a particular clinical trial subject or group of clinical trial subjects, or any other subset of the clinical data stored in the central data repository 626.

In some implementations, the one or more alert systems 666 can provide a clinical trial administrator or other medical professionals with alerts based on predictions from one or more machine learning models described in the system 600. For example, a machine learning model trained to predict a safety signal can trigger an alert if the safety signal exceeds a particular threshold. In some implementations, the alert can lead to a particular automated action. In some other implementations, the alert can be viewed by a particular user, evaluated, and considered as one of many factors for a particular decision or action.

In some implementations, the one or more feedback loops 668 can provide a user an ability to provide feedback that if used for modification of one or more machine learning models, algorithms, or systems described in the system 600. For example, as described in relation to FIG. 4, a clinical trial review center 402 can display one or more predicted signals (e.g., a safety signal and/or efficacy signal) to a user. The user can provide a review to a model updater 410. The model updater 410 can re-train the one or more machine learning models 420 with new training data and/or updated hyperparameters. In addition, the model updater 410 can update the method for determining the predictive features that are processed by the machine learning models 420 and update the method for combining the outputs of the one or more machine learning models 420.

Figure 7:
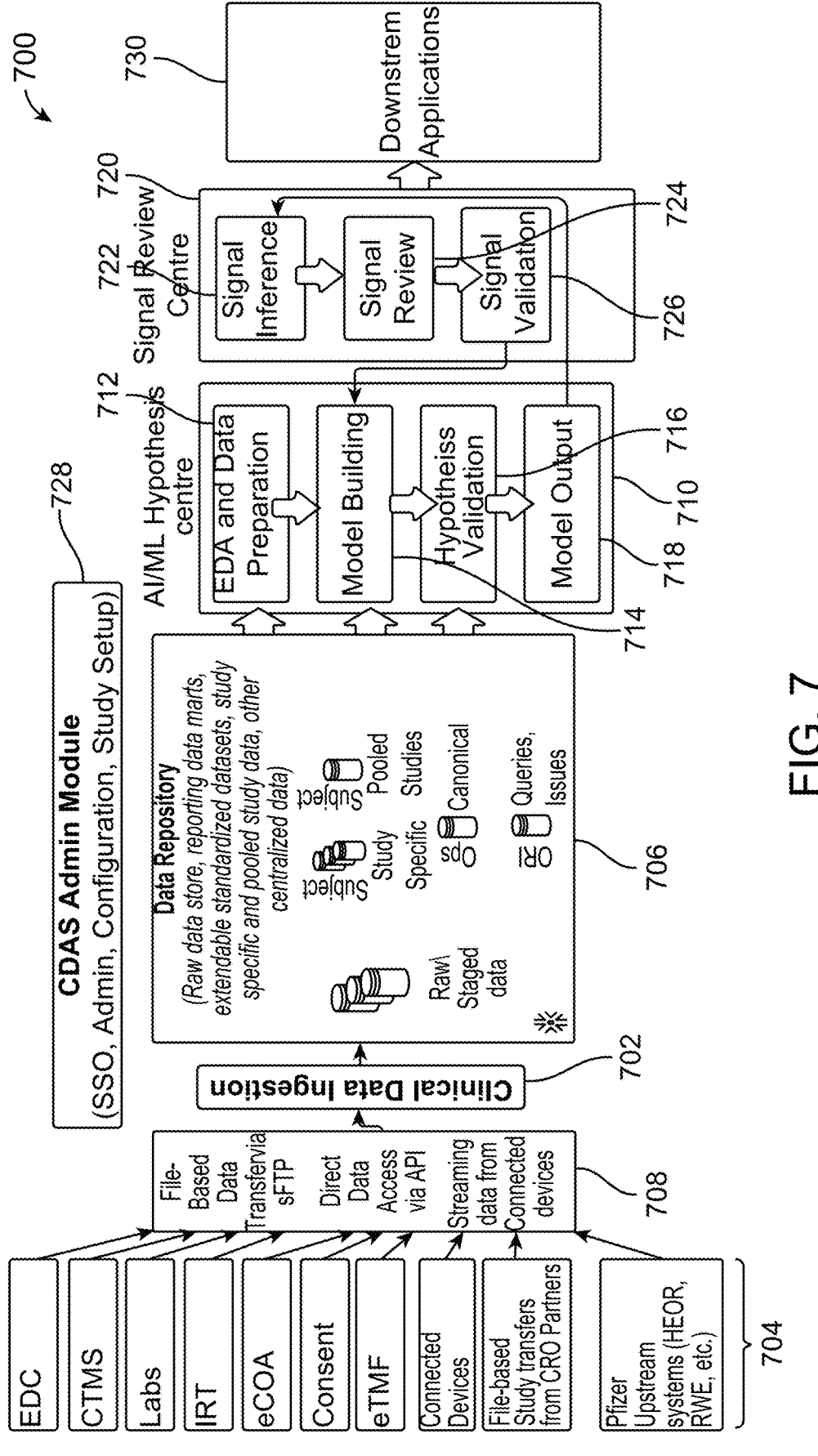
FIG. 7 illustrates an example approach for predicting a safety signal and/or an efficacy signal.

FIG. 7 illustrates an example approach 700 for predicting one or both of a safety signal and an efficacy signal associated with a particular subject of a clinical trial. The approach includes ingesting (702) multiple clinical data sources 704. Data associated with the multiple clinical data sources 704 are collected by one or more data collection techniques 708 and ingested (702) and stored in multiple databases of a data repository 706.

The multiple clinical data sources 704 include data from electronic data capture (EDC) systems, clinical trial management systems (CTMS), laboratory results (e.g., blood tests), interactive response technology (IRT) systems, electronic clinical outcome assessments (eCOA), consent forms, electronic trial master files (eTMF), connected devices, file-based study transfers from associated contract research organizations (CRO) partners, and other upstream systems that may be associated with specific clinical trials.

The data associated from each of the multiple clinical data sources 704 can be collected with multiple techniques including a file-based data transfer through secure file transfer protocol (sFTP), direct data access with application programming interfaces (APIs), streaming data from connected devices, or any other method of transferring data between the multiple clinical trial data sources 704 to the data repository 706.

In some implementations, the data repository 706 includes raw data ingested from the multiple clinical data sources 704, a reporting data mart (e.g., a specialized database designed to facilitate generation of reporting and analysis), extendable standardized datasets (e.g., data that is stored according to a standardized format that can be extended to include new data and new fields without disrupting the existing data of the dataset), study-specific and pooled study data (e.g., data that is organized with respect to a particular clinical trial or group of clinical trials), and other centralized data. In a general sense, the other centralized data includes data that represents attributes of the multiple clinical data sources 704 in a single data structure or multiple combined data structures.

In some implementations, a hypothesis center 710 processes clinical data stored in the data repository 706. For example, the hypothesis center 710 is an example of the system 200 described in relation to FIG. 2. The hypothesis center 710 facilitates exploratory data analysis (EDA) and data preparation step (712) (e.g., operations corresponding to the predictive feature selector 208 and the process of standardization and redaction). The hypothesis center 710 includes a model building step (714) (e.g., operations corresponding to the training system 210) that trains one or more machine learning models (e.g., the machine learning models 220) by processing the set of predictive features. The hypothesis center 710 subsequently executes a hypothesis validation step (716) where a review of the hypothesis is received and the predictive features and/or model architecture are changed if necessary. The hypothesis center 710 generates a model output 718 from the outputs of one or more trained machine learning models.

The output 718 corresponding to a particular clinical trial subject is processed by a signal review center 720 (e.g., the clinical trial review center 710). The signal review center 720 includes a signal inference step (722). The signal inference step (722) includes an interpretation of the model output 718 to generate a more nuanced analysis of the raw model output in conjunction with the predictive features processed by the one or more machine learning models and the associated raw data in relation to the particular clinical trial subject. The signal review center 720 includes a signal review step (724) which can be executed by an automated process or by a medical professional, domain expert, or clinical trial administrator. The signal review center 720 includes a signal validation step (726). The result of the signal review step (724) determines if the signal inferred in 722 is valid or invalid based on a clinical judgement given by the medical professional, domain expert, or clinical trial administrator. The result of the signal validation step (726) is processed by the model building step (714) to adjust one or more parameters of the associated one or more machine learning models or the determination of the selected predictive features, as described in relation to FIG. 4. The output of the signal review center (e.g., the model output 718, the inferred signal from the signal inference step (722), the review from the signal review step (724), and the signal validation result from the signal validation (726) step) is sent to any relevant downstream application 730. In some cases, a relevant downstream application 730 can be a messaging system that alerts relevant personnel of a particular safety or efficacy signal.

In some implementations, the data repository 706, the tool used to ingest (702) clinical data into the data repository 706, and the hypothesis center 710 are managed by a single admin module that includes single sign-on (SSO), administrative functions that controls access to the clinical data and relevant model parameters, and configuration controls through a user interface that provide access to parameters of the clinical data analysis and prediction functions.

Figure 8:
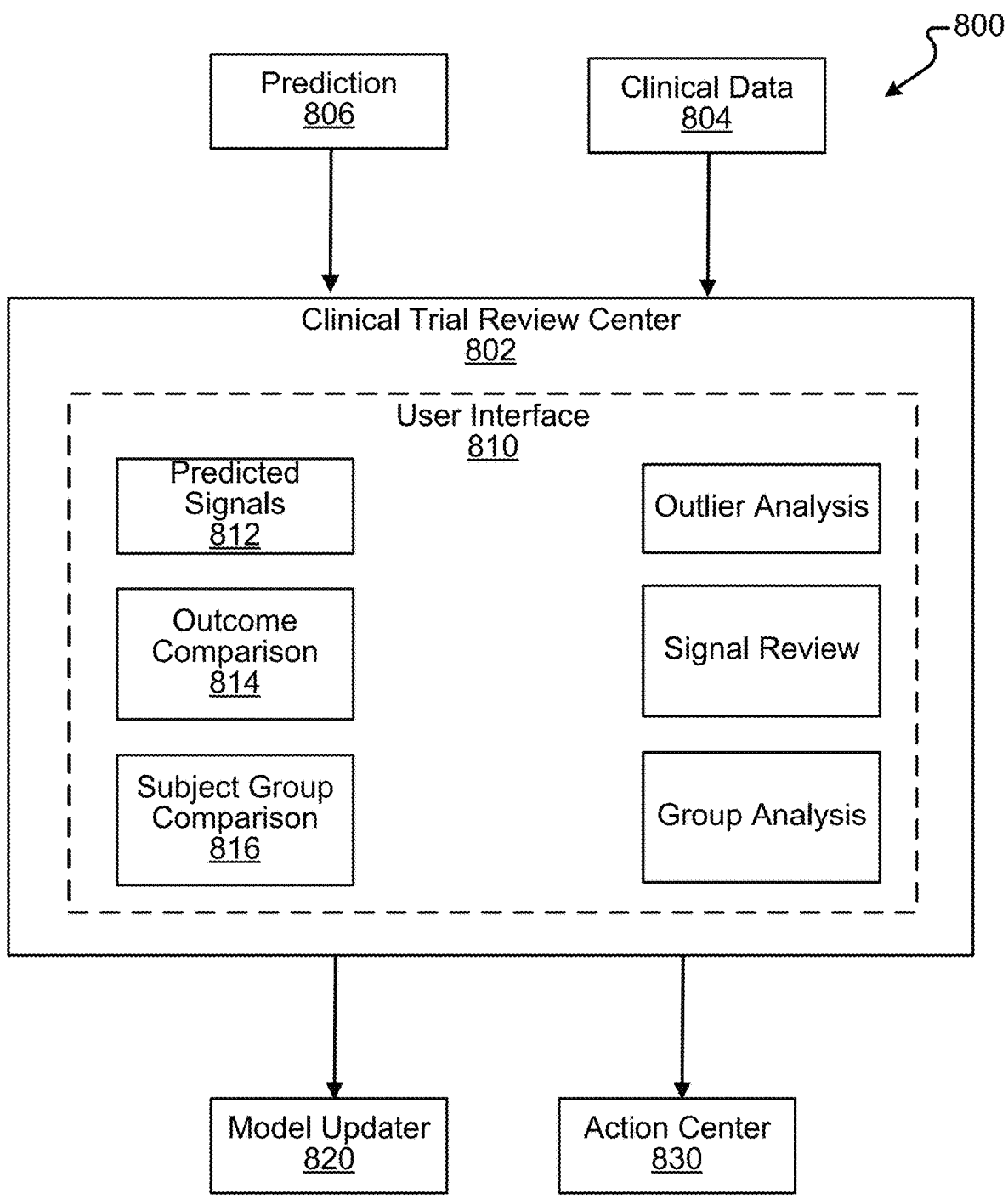
FIG. 8 is a block diagram that illustrates an example of a system that includes a user interface.

FIG. 8 is a block diagram that illustrates an example of a system 800 that includes a user interface 810 to display one or more analyses of clinical data 804 and predictions 806 (e.g., predicted safety and efficacy signals) associated with the clinical data 804. The user interface 810 is implemented on a clinical trial review center 802 that can be accessed by a clinical trial reviewer or other medical professionals associated with managing and administering a related clinical trial.

The clinical trial review center 802 receives one or more predictions 806 and associated clinical data 804. In some cases, the clinical trial review center 802 has access to all clinical data in an associated data repository. For example, the clinical trial review center 802 can include a full-text search engine across multiple data sources like medical journals, redacted electronic health records, adverse event reports, and other documents and data sources that can help a clinical trial reviewer generate a review of the prediction 806 to transmit to a model updater 820 and in some implementations, an action center 830. The action center 830 is one or more decision making resources, including automated computer systems and/or message systems to be processed by medical professionals, that propose actions to be taken in response to the prediction 806 and the corresponding review of the prediction 806 facilitated by the clinical trial review center 802.

The user interface 810 of the clinical trial review center 802 includes multiple graphical representations of the clinical data and how clinical data of a particular clinical trial subject, e.g., adverse events, medications, health outcomes, biomarkers, etc., compares to other groups of clinical trial subjects.

In some implementations, the user interface 810 displays a representation of predicted signals 812 of one or both of the predicted safety signal and efficacy signal associated with the clinical data of the particular clinical trial subject. In some cases, the signals are paired with one or more aspects of the clinical data that are most predictive of the predicted signals. For example, if the predicted safety signal is indicative of the clinical trial being unsafe to continue for the particular clinical trial subject, the predictive safety signal can be accompanied by the associated features responsible for the prediction. For example, an occurrence of an adverse event or specific biomarker trends that are identified through domain expertise to put the particular clinical trial subject at risk.

In some implementations, the user interface 810 displays an outcome comparison 814 between the prediction 806 of the one or more machine learning models (e.g., the output of the model aggregator 304) and observed outcomes represented in the clinical data 804.

In some implementations, the user interface 810 displays a clinical trial subject group comparison 816. The subject group comparison 816 is a graphical display of one or more groups of clinical trial subjects with associated clinical data in the data repository, in which the clinical trial subjects in each of the one or more groups have common clinical characteristics and clinical outcomes. Common clinical characteristics can include similar biomarkers (age, weight, blood type, etc.), and common clinical outcomes can include similar adverse events and responses to treatment.

In some cases, a planning center (e.g., the planning center 214) can include one or more processes and user interfaces to enable the determination of the one or more groups of clinical trial subjects. In addition, the analysis of the one or more groups of clinical trial subjects in the clinical trial review center 802 can provide indicators and feedback that can be processed by the model updater 820 to modify the one or more predictive features to improve the predictive ability of the one or more trained machine learning models. The user interface 810 can graphically display the characteristics (e.g., biomarkers, clinical data attributes, etc.) of the particular clinical trial subject in relation to other clinical trial subjects of a particular group (e.g., a cluster of clinical trial subjects based on one or more characteristics).

In some implementations, the user interface 810 displays an outlier analysis that identifies characteristics and attributes of the particular clinical trial subject that are outside of a particular range from what is expected for a clinical trial subject associated with the particular attributes.

In some implementations, the user interface 810 displays a signal review. The signal review displays a safety signal and/or an efficacy signal. In addition to the signal, which in some implementations is a numerical indicator within a pre-defined scale, the signal review includes the one or more features of the clinical data that contributed the most to the predicted signal. For example, if a particular safety signal is indicative of a high likelihood of an adverse event for a particular clinical trial subject, the signal review can include the one or more predictive features (e.g., particular biomarkers) that are the strongest indicators that the predictions is valid.

In some implementations, the user interface 810 displays a group analysis. The group analysis can provide an illustration of one or more characteristics of a particular clinical trial subject in relation to multiple other clinical trial subjects. In some cases, the multiple other clinical trial subjects participate in different clinical trials. In some cases, the multiple other clinical trial subjects participate in the same, potentially ongoing, clinical trial as the particular clinical trial subject. By comparing the clinical characteristics of the particular clinical trial subject with other subjects that have similar clinical characteristics, a user, through the user interface 810, can determine if the particular clinical trial subject is responding to a treatment in a similar way compared to other similar clinical trial subjects.

Figure 9:
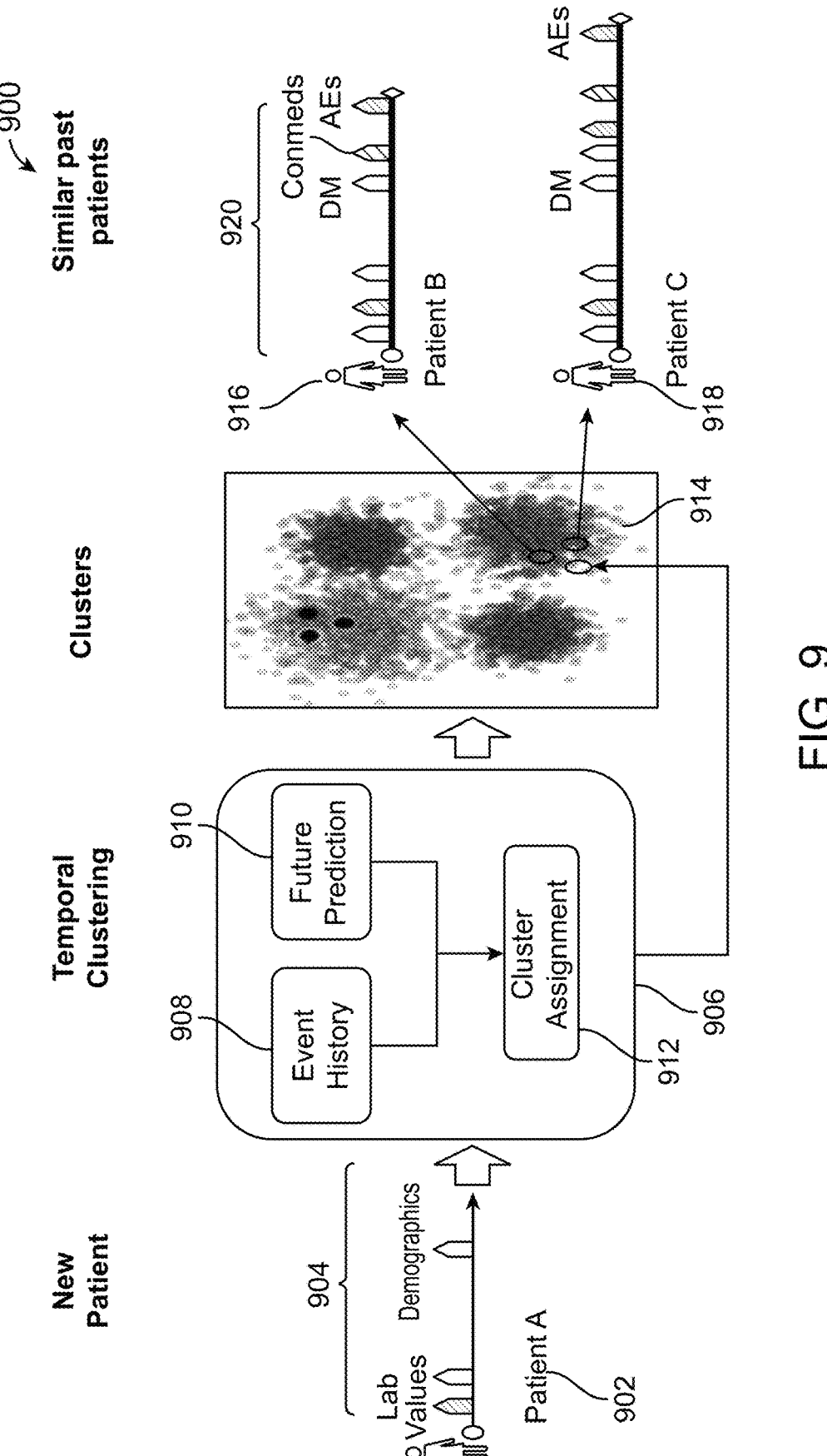
FIG. 9 illustrates an example approach for identifying past clinical trial subjects.

FIG. 9 illustrates an example approach 900 for determining similar past clinical trial subjects (e.g., clinical trial subject 916 and clinical trial subject 918) as a particular clinical trial subject 902 based on shared characteristics.

Clinical trial sites can collect data from clinical trial subjects (patients) over time as the clinical trial proceeds. For example, when the clinical trial begins, the clinical trial site has little clinical data about the clinical trial subjects related to the clinical trial. However, upon commencement, data including demographics, key biomarkers revealed by blood tests and imaging, and other baseline characteristics are known to the administrators of the clinical trial. As the clinical trial treatment is delivered, new data is generated such as lab visits, new blood work, new medications, treatment outcomes, adverse events, etc. The presence and details of these data along with the temporal relationship between them provide information to group (e.g., cluster) clinical trial subjects along various dimensions.

As an illustrative example, consider the particular clinical trial subject 902 that is previously unknown to the clinical trial administrators. In some cases, demographic data and past lab results can establish a baseline characteristic timeline 904 associated with the particular clinical trial subject 902. A temporal clustering process 906 can process the baseline characteristic timeline 904 (e.g., event history 908) along with one or both of a predicted safety signal and a predicted efficacy signal, as described in relation to previous figures. The temporal clustering process 906 can assign the particular clinical trial subject 902 to a particular cluster 914, in which the particular cluster 914 includes additional clinical trial subjects (e.g., clinical trial subjects 916-918) with similar baseline characteristic timelines 920 and similar observed outcomes compared to the predictions associated with the particular clinical trial subject 902.

Figure 10:
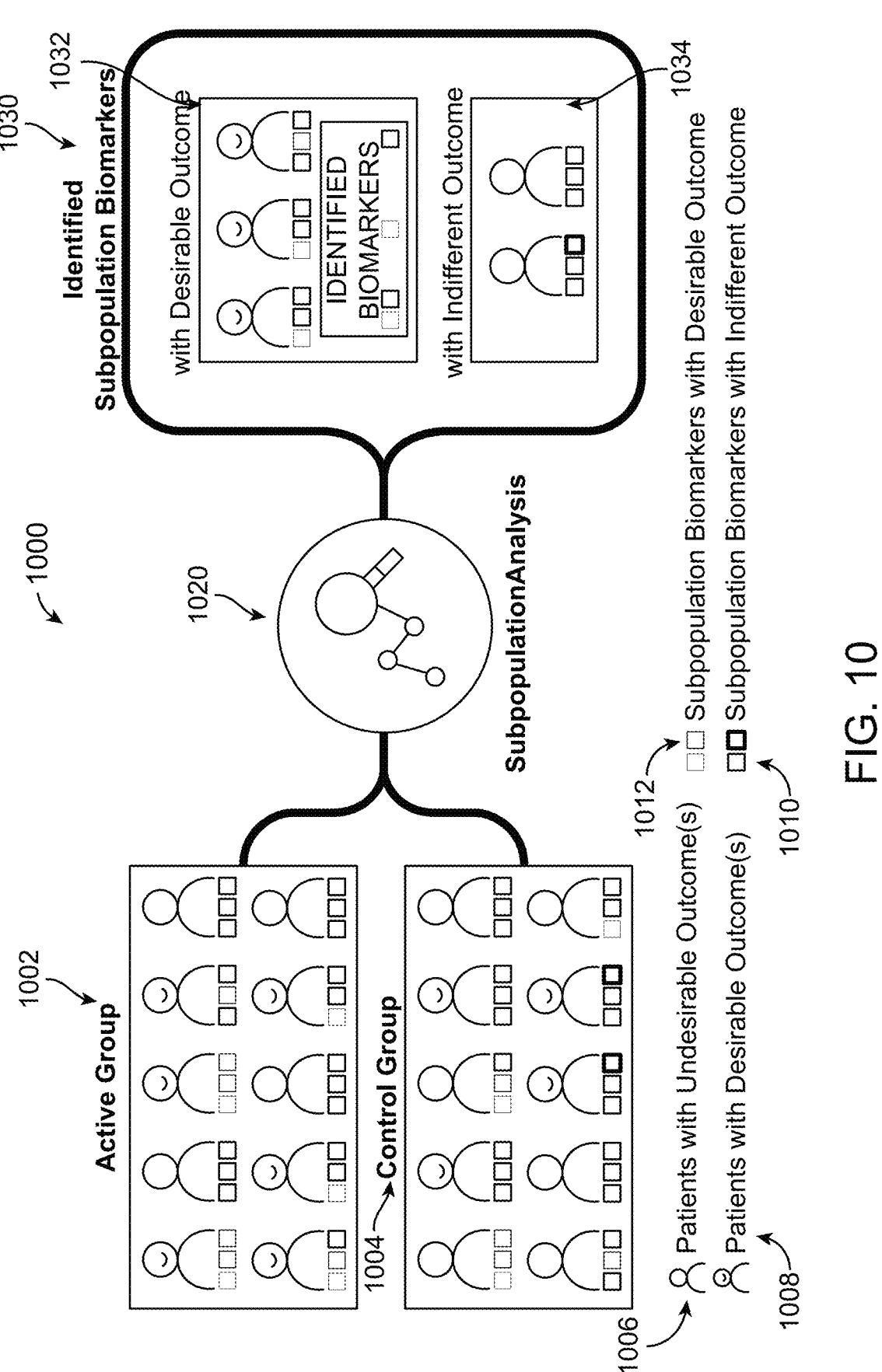
FIG. 10 illustrates an example approach for analyzing a subgroup of clinical trial subjects.

FIG. 10 illustrates an example approach 1000 for analyzing a subgroup of clinical trial subjects. The approach 1000 includes a dual-arm analysis (e.g., an analysis that includes an active group and a control group) of clinical trial subjects to determine one or more predictive features that have stronger outcomes (e.g., strong correlation with a desirable outcome) for a first group of clinical trial subjects compared to a second group of clinical trial subjects.

In some implementations, a subpopulation analysis module 1020 processes clinical trial data (e.g., clinical characteristics like biomarkers), from two groups of clinical trial subjects. The first group of clinical trial subjects represents an active group 1002 of clinical trial subjects. The second group of clinical trial subjects represents a control group 1004 of clinical trial subjects. The active group 1002 includes clinical trial subjects that receive treatment from a particular clinical trial. The control group 1004 includes clinical trial subjects that do not receive treatment from the particular clinical trial.

In some implementations, each clinical trial subject in the active group 1002 and the control group 1004 is characterized by a desirable outcome 1006 or an undesirable outcome 1008. The outcomes 1006-1008 can be determined by an occurrence of an adverse event or some other indicator of an undesirable event. In addition, each clinical trial subject in both groups 1002-1004 may be characterized by one or more first biomarkers 1012 that correlate with a desirable outcome and/or one or more second biomarkers 1010 that correlate with an indifferent outcome. In this case, a biomarker that correlates with an indifferent outcome has no predictive value in relation to the outcome.

In some implementations, the subpopulation analysis module 1020 is one or more trained machine learning models. The one or more trained machine learning model is trained on clinical data (e.g., clinical data stored in the data repository 206). The training data includes multiple biomarkers and clinical characteristics of multiple clinical trial subjects with associated outcomes (e.g., both desirable and undesirable outcomes). The one or more machine learning models are trained to predict the presence of a desirable outcome, or an undesirable outcome based on patterns in the stored clinical data. The method for training the one or more machine learning models is similar to the method described in relation to FIG. 2.

The subpopulation analysis module 1020 can cluster the input clinical trial subjects that includes both the active group 1002 and the control group 1004 into a first group and a second group along with one or more identified subpopulation biomarkers 1030. In some implementations, the first group 1032 represents clinical trial subjects that exhibit desirable outcomes, and the second group 1034 represents clinical trial subjects that exhibit indifferent outcomes. The biomarkers that characterize the first group 1032 represent the one or more first biomarkers 1012 that are predictive features for predicting a likelihood of a desirable outcome for a particular clinical trial subject. The biomarkers that characterize the second group 1034 represent the one or more second biomarkers 1010 that are not predictive features for predicting a likelihood of a desirable outcome for the particular clinical trial subject.

In some implementations, the subpopulation analysis module 1020 is a component of a planning center (e.g., the planning center 214) that includes a user interface and enables a user (e.g., a clinical trial administrator or medical professional) to determine the one or more predictive features for a particular population of clinical trial subjects.

Figure 11:
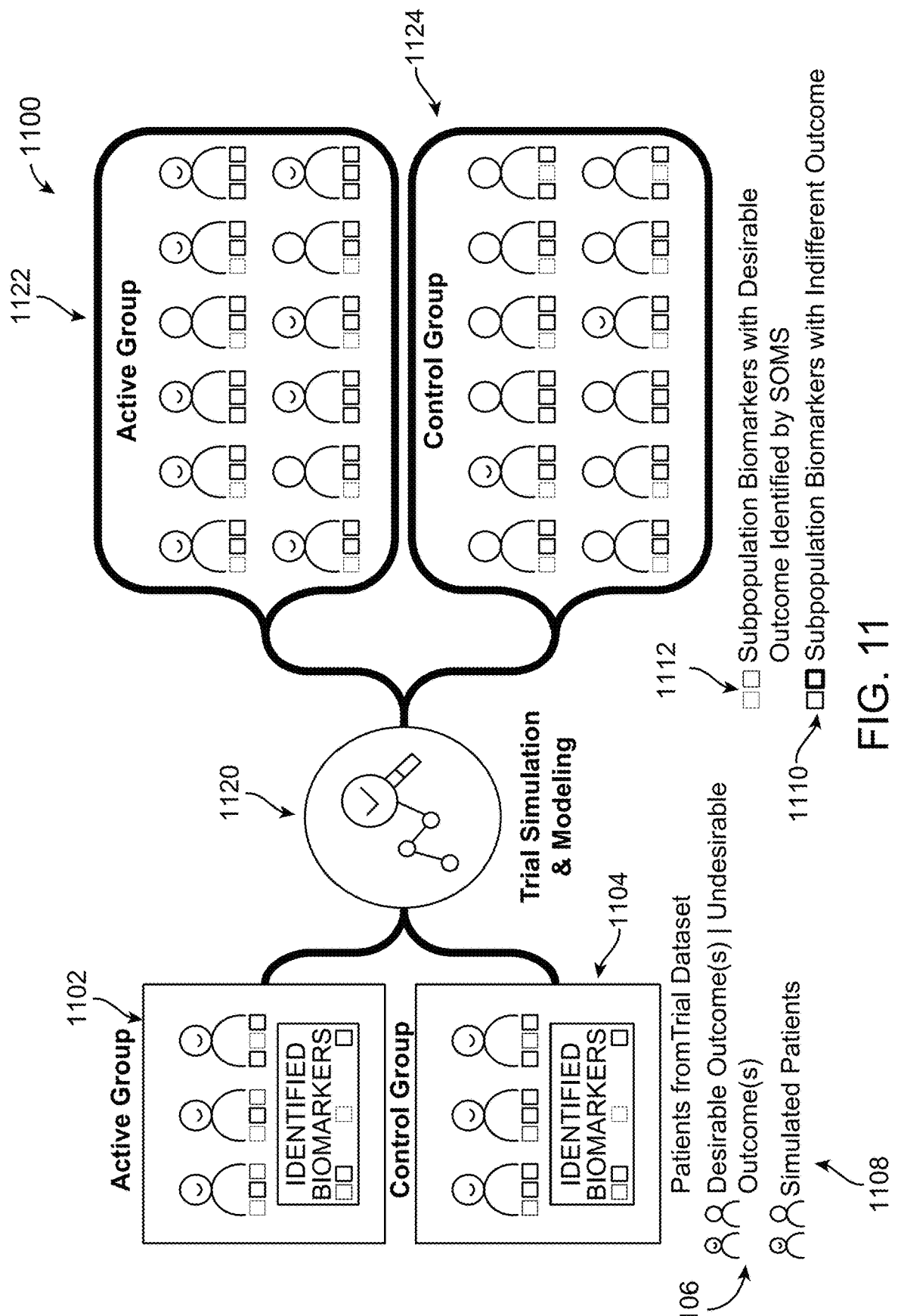
FIG. 11 illustrates an example approach for generating simulated clinical trial data.

FIG. 11 illustrates an example approach 1100 for generating simulated clinical trial data. The approach 1100 includes a trial simulation and modeling module 1120 that processes clinical data corresponding to an active group 1102 of clinical trial subjects and a control group 1104 of clinical trial subjects. In some implementations, the trial simulation and modeling module 1120 includes one or more trained machine learning models that are trained on clinical data associated with multiple clinical trial subjects (e.g., the clinical data stored in the data repository 206).

The active group 1102 of clinical trial subjects includes clinical trial subjects that exhibit a desirable outcome. For example, the active group 1102 is similar to the first group 1032 represented in FIG. 10 that corresponds to the one or more first biomarkers 1012. In some implementations, the active group 1102 of clinical trial subjects includes one or more clinical trial subjects that exhibit indifferent outcomes.

The control group 1104 of clinical trial subject includes both clinical trial subjects that exhibit desirable outcomes and clinical trial subjects that exhibit indifferent outcomes. In both cases (e.g., the active group 1102 and the control group 1104), the clinical data associated with the respective clinical trial subjects is represented in the clinical data stored in a data repository (e.g., the data repository 206), in relation to real clinical trial subjects.

In some implementations, the trial simulation and modeling module 1120 processes the active group 1102 and the control group 1104 and determines a first simulated group and a second simulated group of clinical trial subjects, in which each simulated group of clinical trial subjects includes more clinical trial subjects than the active group 1102 and the control group 1104. The first simulated group of clinical trial subjects represents a simulated active group 1122. The second simulated group of clinical trial subjects represents a simulated control group 1124. The simulated active group 1122 includes multiple simulated clinical trial subjects, in which each simulated clinical trial subject is associated with one or more biomarkers and an indicator that represents a desirable outcome or an indifferent outcome.

The relationship between the biomarkers and the outcomes between the clinical trial subjects of the input groups (e.g., the active group 1102 and the control group 1104) and the simulated output groups (e.g., the simulated active group 1122 and the simulated control group 1124) is preserved through the transformation provided by the trial simulation and modeling module 1120. For example, a clinical trial subject in the simulated active group 1122 that exhibits one or more first biomarkers 1112 exhibits a desirable outcome. Similarly, a clinical trial subject in the simulated control group 1124 that exhibits one or more second biomarkers 1110 exhibits an indifferent outcome. In other words, the biomarkers of the simulated clinical trial subjects exhibit the same predictive qualities with respect to a clinical trial outcome as the biomarkers associated with the real clinical trial subjects.

FIG. 12 displays an example user interface 1200 for analyzing subgroups of clinical trial subjects. In some implementations, a planning center (e.g., the planning center

214 of FIG. 2) includes a user interface that displays a subgroup analysis of clinical data related to multiple clinical trial subjects.

In some implementations, the user interface 1200 includes a table 1202 that displays information about multiple subgroups of clinical trial subjects. For example, the table 1202 includes, for each subgroup, a definition of the subgroup, the size of the subgroup, the splitting criterion of the subgroup (e.g., a metric used to divide the group into multiple subgroups), and the multiplicity adjusted outcome difference p-value (e.g., a p-value that has been adjusted for cases with multiple comparisons). For example, the highlighted group 1204 indicates the associated subgroup of clinical trial subjects includes clinical trial subjects with a diastolic blood pressure above 92.5 and a history of metabolism and nutrition disorders. The mean outcome indicator displayed in table 1210 for the highlighted group 1204 is 0.1, which indicates subjects of the highlighted group 1204 had less improvement with respect to a particular treatment that the overall population of clinical trial subjects (e.g., the mean outcome indicator displayed in 1210 for the overall population of clinical trial subjects is −0.8).

In some implementations, the user interface 1200 includes a histogram 1220 that indicates the relative importance of multiple biomarkers (e.g., blood pressure, age, height, etc.) in the prediction of a particular outcome. The histogram 1220 displays a relative variable importance score for a set of biomarkers that includes diastolic blood pressure, age, height, weight, heart rate, and a history of vascular disorders. As shown by the longest bar in the histogram, the diastolic blood pressure is the biomarker with the most predictive value compared to the other biomarkers displayed in the histogram 1220.

In some implementations, the user interface 1200 includes a scatterplot 1230 for each biomarker that indicates the distribution of each biomarker with respect to an outcome indicator. In some implementations, the scatterplot 1230 includes an associated filter in which a user can select a particular sub-population or subgroup of clinical trial subjects to analyze. For example, the distribution of a particular biomarker may be different for a first subgroup compared to a second subgroup. In other words, a biomarker may be a strong predictive feature for the first group of clinical trial subjects with similar characteristics and a weak predictive feature for the second group of clinical trial subject with similar characteristics to each other but different from the first group.

Figure 13:
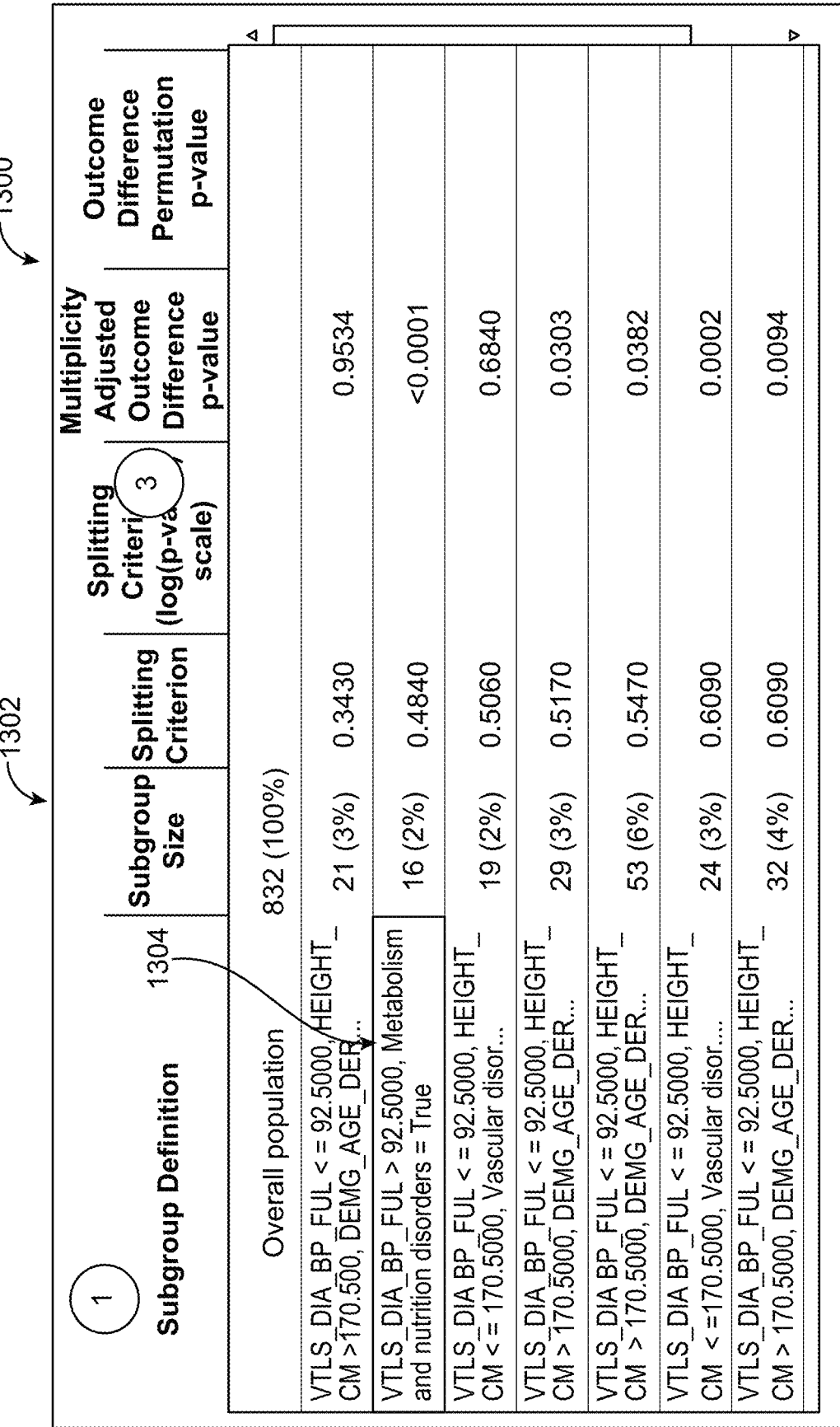
FIG. 13 displays an example user interface.

FIG. 13 displays an example user interface 1300 for analyzing subgroups of clinical trial subjects. In some implementations, a planning center (e.g., the planning center 214 of FIG. 2) includes components of the user interface 1300 that displays subgroup analysis of clinical data related to multiple clinical trial subjects. In some implementations, a clinical trial review center (e.g., the clinical trial review center 402 of FIG. 4) includes components of the user interface 1300.

In some implementations, a clinical trial reviewer interacts with the user interface 1300 to review and validate predicted signals (e.g., the prediction 406) to determine if the signal is valid based on the domain expertise of the clinical trial reviewer. In some cases, the review provided by the clinical trial reviewer, enabled by the data displayed on the user interface 1300, can be used to update one or more machine learning models (e.g., the machine learning models 420), one or more predictive features for one or more subgroups of clinical trial subjects, or the method of aggregation of outputs from more than one machine learning model.

In some implementations, the user interface 1300 includes a table 1302 that displays information about multiple subgroups of clinical trial subjects. For example, the table 1302 includes, for each subgroup, a definition of the subgroup, a size of the subgroup, a splitting criterion of the subgroup (e.g., a metric used to divide the group into multiple subgroups), and a multiplicity adjusted outcome difference p-value (e.g., a p-value that has been adjusted for cases with multiple comparisons). For example, the highlighted group 1304 indicates the associated subgroup of clinical trial subjects includes clinical trial subjects with a diastolic blood pressure between 88.5 and 92.5. The mean outcome indicator displayed in table 1310 for the highlighted group 1304 is −0.5, which indicates subjects of the highlighted group 1304 had less improvement with respect to a particular treatment that the overall population of clinical trial subjects (e.g., the mean outcome indicator displayed in 1310 for the overall population of clinical trial subjects is −0.8).

In some implementations, the user interface 1300 includes a heatmap 1340 that displays information about the multiple subgroups of clinical trial subjects represented in the table 1302. The heatmap 1340 includes a first heatmap 1342, a second heatmap 1344, and a third heatmap 1346.

The first heatmap 1322 displays a distribution of clinical characteristics of clinical trial subjects for multiple subgroups. For example, the first heatmap 1342 displays an average age for each subgroup of clinical trial subjects, an average body mass index (BMI) for each subgroup of clinical trial subjects, and for each subgroup of clinical trial subjects, a percentage of clinical trial subjects that have been previously admitted to an intensive care unit (ICU).

The second heatmap 1344 displays a distribution of clinical characteristics of clinical trial subjects for multiple subgroups, in which the clinical characteristics are related to measurements and/or observations received during a clinical examination. For example, the second heatmap 1344 displays an average heartrate for each subgroup of clinical trial subjects, a tidal volume for each subgroup of clinical trial subjects, and a respiratory rate of each subgroup of clinical trial subjects.

The third heatmap 1346 displays a distribution of clinical characteristics of clinical trial subjects for multiple subgroups, in which the clinical characteristics are related to co-morbidities and medical history. For example, the third heatmap 1346 displays a percentage of clinical trial subjects in each group of clinical trial subjects with a history of cirrhosis, a percentage with a history of respiratory insufficiency, and a history of immune insufficiency.

The heatmaps 1342-1346 provide a visual representation of clinical characteristics across clinical trial subjects of multiple groups. The visual representation can assist a clinical trial reviewer, or a clinical trial administrator determine one or more predictive features (e.g., one of the clinical characteristics or a combination of more than on clinical characteristics displayed in the heatmaps 1342-1346).

In some implementations, the user interface 1300 includes a histogram 1320 that indicates the relative importance of multiple biomarkers (e.g., blood pressure, age, height, etc.) in the prediction of a particular outcome. The histogram 1320 displays a relative variable importance score for a set of biomarkers that includes weight, diastolic blood pressure, temperature, height, and heart rate. As shown by the longest bar in the histogram, the weight of the clinical trial subject is the biomarker with the most predictive value compared to the other biomarkers displayed in the histogram 1320.

In some implementations, the user interface 1300 includes a scatterplot 1330 for each biomarker that indicates the distribution of each biomarker with respect to an outcome indicator. In some implementations, the scatterplot 1330 includes an associated filter in which a user can select a particular sub-population or subgroup of clinical trial subjects to analyze. For example, the distribution of a particular biomarker may be different for a first subgroup compared to a second subgroup. In other words, a biomarker may be a strong predictive feature for a first group of clinical trial subjects with similar characteristics and a weak predictive feature for a second group of clinical trial subject with similar characteristics to each other but different from the first group.

In some implementations, the user interface 1300 includes a timeline 1350 that represents an administration of one or more concomitant medications for a particular clinical trial subject. A particular clinical trial may include one or more treatments or therapeutics as part of the clinical trial protocol. However, in some cases, a particular clinical trial subject may receive additional treatments or therapeutics for pre-existing and/or unrelated conditions relative to the clinical trial. The timeline 1350 enables a clinical trial reviewer or clinical trial administrator to analyze the relative timing between all treatments and therapeutics for the particular clinical subject to correlate with any potential adverse events and/or potential changes in safety and/or efficacy.

In some implementations, the timeline 1350 indicates one or more treatments (e.g., multivitamin 1352) received and the timing with which the particular clinical trial subject received it. In addition, the timeline 1350 indicates one or more adverse events (e.g., adverse event 1354) by a vertical line. The adverse event 1354 indicates a mild adverse event occurred around the seventeenth day of the clinical trial and it coincided with the beginning of a time period over which the particular clinical trial subject began to receive Vicks formula.

FIG. 14 displays an example comparison of multiple machine learning models that generate an efficacy signal prediction. The table 1402 compares a precision 1404, a sensitivity 1406, an F1 score 1408, and an accuracy 1410 for three machine learning models that include CaRT Tree model 1420, a first CaRT RF model 1422, and a second CaRT RF model 1424. The models 1420-1424 are trained to predict if each clinical trial subject will have a reduction in pain over the course of a clinical trial.

The CaRT Tree model 1420 is a machine learning model used for classification and regression tasks. The CaRT Tree model 1420 is a single decision tree that splits the data into branches to make predictions. The splits are made based on feature values that best separate the classes or predict the target variable.

The first and second CaRT RF models 1422-1424 are machine learning model that includes a random forest ensemble method that includes many decision trees (e.g., a "forest") to make predictions. Each tree in the forest is built from a random sample of the data, and they make decisions collectively.

In this example, the CaRT Tree model 1420 is trained on clinical data that includes subject demographics, vitals, medical history, concomitant medications, and pain scores. The first CaRT RF model 1422 is trained on clinical data that includes subject demographics, vitals, medical history, concomitant medications, and pain scores from a n visits (e.g., from a first n visits to a clinical trial site or a first n visits to a clinician in relation to the treatment provided by the clinical trial protocol). The second CaRT RF model 1424 is trained on clinical data that includes subject demographics, vitals, medical history, concomitant medications, and a change in pain from baseline to a first n visits.

The parameters that characterize each machine learning model displayed in the table 1402 can be used to differentiate the type of models and the corresponding training data used to train the different types of models. The precision 1404 column represents the proportion of correct positive identifications. A model with high precision has a low rate of false positives. The sensitivity 1406 column represents the proportion of correctly identified positive identifications. A model with a high sensitivity has a high rate of positive detection. The F1 score 1408 column represents a harmonic mean of the precision and the sensitivity, providing a balanced view of the performance of a model. In some cases, both precision and sensitivity are important, so the F1 score is a useful parameter to consider when choosing a machine learning model for a particular task. The accuracy 1410 column represents the proportion of all predictions that the model correctly identified, both positive and negative.

As illustrated in the table 1402, the first CaRT RF model 1422 exhibits the highest precision and the highest accuracy. However, the second CaRT RF model 1424 exhibits the highest F1 score and sensitivity by a large margin. The data illustrated in table 1402 demonstrates how a medical professional or clinical trial administrator can review model comparisons to determine an appropriate model, group of models, and training data to use for a particular efficacy signal prediction.

FIG. 15 displays an example comparison of multiple machine learning models that generate an safety signal prediction. The table 1502 compares a precision 1504, a sensitivity 1506, an F1 score 1508, and an accuracy 1510 for three machine learning models that include a first CaRT RF model 1522 and a second CaRT RF model 1524. The models 1522-1524 are trained to predict if each clinical trial subject will experience an adverse event over the course of a clinical trial.

As described in relation to FIG. 14, the first and second CaRT RF models 1522-1524 are machine learning model that includes a random forest ensemble method that includes many decision trees (e.g., a "forest") to make predictions. Each tree in the forest is built from a random sample of the data, and they make decisions collectively.

In this example, the first CaRT RF model 1522 is trained on clinical data that includes subject demographics, vitals, medical history, concomitant medications, and change in pain from baseline to a first n visits. The second CaRT RF model 1524 is trained on clinical data that includes subject demographics, vitals, medical history, concomitant medications, and change in pain from baseline to a first n visits. The second CaRT RF model 1524 is trained using only one tree. In this example, both models 1522-1524 are trained using the same training data, but the architecture of the models are different.

As described in relation to FIG. 14, the parameters that characterize each machine learning model displayed in the table 1502 can be used to differentiate the type of models and the corresponding training data used to train the different types of models.

As illustrated in the table 1502, the first CaRT RF model 1522 exhibits the highest precision. However, the second CaRT RF model 1524 exhibits the highest F1 score and sensitivity by a large margin. The data illustrated in table 1502 demonstrates how a medical professional or clinical trial administrator can review model comparisons to determine an appropriate model, group of models, and training data to use for a particular efficacy signal prediction.

In some implementations, the techniques described in this specification can be performed by a machine learning model. The model may adjust a penalty parameter and in some implementations, parameters adjusted in the model can be learned e.g., by a neural network that can include the model. In some implementations, model parameters adjusted for the model can include coefficients or weights of a neural network, biases of a neural network, and cluster centroids in clustering networks. In some implementations, hyperparameters e.g., parameters to adjust learning of the model, can be adjusted for training the model. Hyperparameters may include a test-train split ratio, learning rates, selection of optimization algorithms, selection of functions e.g., activation, cost, or loss functions, a number of hidden layers, a dropout rate, a number of iterations, a number of clusters, a pooling size, a batch size, and a kernel or filter size in convolutional layers.

The model can use any appropriate algorithm such as backpropagation of error or stochastic gradient descent for training. Through many different training iterations, based on training data and examples provided to the model, the model learns to accurately estimate sources of non-compliance. The model can be trained on multiple sets of documents from clinical sites. The model is evaluated for error and accuracy over a validation set. The model training continues until either a timeout occurs, e.g., typically several hours, or a predetermined error or accuracy threshold is reached. In some implementations, an ensemble approach of models may be implemented by the model to improve overall accuracy of non-compliance in documents. Model training and re-training of the model can be performed repeatedly at a pre-configured cadence e.g., once a week, once a month, and if new data is available in the object store then it automatically gets used as part of the training. The data pipeline to obtain new data remains the same as described above.

In some implementations, the model can include feed-forward neural networks with multiple feed-forward layers. Each feed-forward neural network can include multiple fully-connected layers, in which each fully-connected layer applies an affine transformation to the input to the layer, i.e., multiplies an input vector to the layer by a weight matrix of the layer. Optionally, one or more of the fully-connected layers can apply a non-linear activation function e.g., ReLU, logistic, hyperbolic tangent, to the output of the affine transformation to generate the output of the layer. In some implementations, the model can include regression e.g., linear, logistic, polynomial, ridge, LASSO techniques.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them. The computer storage medium is not, however, a propagated signal.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

While this specification contains specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method for detecting signals related to subjects participating in a clinical trial, the method comprising:
collecting clinical data for patients from a plurality of sources, the clinical data from each source having a respective data format;
standardizing the clinical data from the plurality of sources in a common format and redacting personally identifiable information from the clinical data;
storing the standardized and redacted clinical data in a data repository;
determining one or more predictive features, wherein each predictive feature corresponds to one or more characteristics of the stored clinical data that correlate with a safety signal for the patients;

obtaining, from the stored clinical data, training data including one or more predictive features and associated safety signal;
using the training data to train one or more machine learning models to predict a predicted safety signal for a clinical trial subject based on clinical data for the clinical trial subject;
receiving clinical data for a particular clinical trial subject enrolled in an ongoing clinical trial;
by the trained machine learning models, predicting a particular safety signal for the particular clinical trial subject based on one or more predictive features determined from the received clinical data for the particular clinical trial subject;
receiving, through a user interface, a review of the particular safety signal; and
updating the one or more trained machine learning models based on the review, including (i) re-training one or more of the trained machine learning models using updated training data, (ii) re-determining one or more of the predictive features based on the review, and (iii) re-training one or more of the trained machine learning models with an updated set of corresponding hyperparameters.

2. The method of claim 1, comprising determining one or more of the predictive features by identifying one or more characteristics of the stored clinical data that correlate with a safety signal associated with a population of clinical trial subjects.

3. The method of claim 2, wherein the characteristics comprise one or more biomarkers.

4. The method of claim 1, wherein re-determining the one or more predictive features comprises updating a relative importance of one or more predictive features compared to the other predictive features.

5. The method of claim 1, wherein re-training one or more of the trained machine learning models with an updated set of corresponding hyperparameters comprises implementing one or more automated algorithms to determine an updated set of hyperparameters.

6. The method of claim 1, comprising presenting, through the user interface, information indicative of the predicted safety signal for the clinical trial subject, the information sufficient to enable intervention in care received by the clinical trial subject through the ongoing clinical trial.

7. The method of claim 1, comprising presenting, through the user interface, information indicative of a comparison of model prediction and observed outcomes for one or more particular clinical trial subjects.

8. The method of claim 1, comprising:
training one or more other machine learning models using the training data; and
simulating, using the trained other machine learning models, one or more expected outcomes of a future clinical trial, wherein the relationship between characteristics of clinical data associated with the future clinical trial is similar to the relationship between the characteristics of the stored clinical data associated with one or more clinical trials.

9. The method of claim 1, wherein the clinical data includes clinical trial data, non-clinical trial health data, synthetic clinical trial data, and synthetic non-clinical trial health data.

10. The method of claim 1, further comprising determining one or more groups of clinical trial subjects with associated clinical data in the data repository, wherein the clinical trial subjects in each of the one or more groups have common clinical characteristics and clinical outcomes.

11. The method of claim 10, further comprising updating one or more of the predictive features for the clinical trial subject based on one or more of the groups to which the subject belongs.

12. The method of claim 10, comprising presenting, through the user interface, one or more interactive graphical representations of the clinical data of the particular clinical trial subject in relation to clinical data of clinical trial subjects in one or more of the groups.

13. The method of claim 1, comprising presenting, through the user interface, information indicative of one or more safety signals, the information sufficient to terminate the ongoing clinical trial.

14. The method of claim 1, further comprising presenting, through the user interface, information enabling real-time oversight of the ongoing clinical trial.

15. The method of claim 10, comprising presenting, through the user interface, information indicative of whether the particular clinical trial subject of the ongoing clinical trial is an outlier in relation to clinical trial subjects in one or more of the groups of clinical trial subjects.

16. The method of claim 1, comprising presenting, through the user interface, information indicative of a comparison of clinical data related to clinical trial subjects of the ongoing clinical trial with clinical data related to one or more clinical trials from the clinical data stored in the data repository.

17. The method of claim 1, comprising presenting, through the user interface, information indicative of one or more reviews of raw clinical data, predicted safety signals, and predicted efficacy signals related to one or more clinical trial subjects of the ongoing clinical trial.

18. The method of claim 10, comprising presenting, through the user interface, information indicative of one or more groups of clinical trial subjects, each group comprising clinical trial subjects with similar clinical characteristics including demographics, medical history, and treatment outcomes.

19. A system for detecting signals related to subjects participating in a clinical trial, the system comprising:
   at least one processor; and
   a memory storing instructions that, when executed by the at least one processor, cause the at least one processor to perform operations comprising:
      collecting clinical data for patients from a plurality of sources, the clinical data from each source having a respective data format;
      standardizing the clinical data from the plurality of sources in a common format and redacting personally identifiable information from the clinical data;
      storing the standardized and redacted clinical data in a data repository;
      determining one or more predictive features, wherein each predictive feature corresponds to one or more characteristics of the stored clinical data that correlate with a safety signal for the patients;
      obtaining, from the stored clinical data, training data including one or more predictive features and associated safety signal;

using the training data to train one or more machine learning models to predict a predicted safety signal for a clinical trial subject based on clinical data for the clinical trial subject;
      receiving clinical data for a particular clinical trial subject enrolled in an ongoing clinical trial;
      by the trained machine learning models, predicting a particular safety signal for the particular clinical trial subject based on one or more predictive features determined from the received clinical data for the particular clinical trial subject;
      receiving, through a user interface, a review of the particular safety signal; and
      updating the one or more trained machine learning models based on the review, including (i) re-training one or more of the trained machine learning models using updated training data, (ii) re-determining one or more of the predictive features based on the review, and (iii) re-training one or more of the trained machine learning models with an updated set of corresponding hyperparameters.

20. One or more non-transitory computer readable media storing instructions that, when executed by at least one processor, cause the at least one processor to detect signals related to subjects participating in a clinical trial by performing operations comprising:
   collecting clinical data for patients from a plurality of sources, the clinical data from each source having a respective data format;
   standardizing the clinical data from the plurality of sources in a common format and redacting personally identifiable information from the clinical data;
   storing the standardized and redacted clinical data in a data repository;
   determining one or more predictive features, wherein each predictive feature corresponds to one or more characteristics of the stored clinical data that correlate with a safety signal for the patients;
   obtaining, from the stored clinical data, training data including one or more predictive features and associated safety signal;
   using the training data to train one or more machine learning models to predict a predicted safety signal for a clinical trial subject based on clinical data for the clinical trial subject;
   receiving clinical data for a particular clinical trial subject enrolled in an ongoing clinical trial;
   by the trained machine learning models, predicting a particular safety signal for the particular clinical trial subject based on one or more predictive features determined from the received clinical data for the particular clinical trial subject;
   receiving, through a user interface, a review of the particular safety signal; and
   updating the one or more trained machine learning models based on the review, including (i) re-training one or more of the trained machine learning models using updated training data, (ii) re-determining one or more of the predictive features based on the review, and (iii) re-training one or more of the trained machine learning models with an updated set of corresponding hyperparameters.

* * * * *